(12) United States Patent
Greener et al.

(10) Patent No.: US 11,701,263 B2
(45) Date of Patent: Jul. 18, 2023

(54) WOUND DRESSING

(71) Applicant: Smith & Nephew, Inc., Memphis, TN (US)

(72) Inventors: Bryan Greener, York (GB); Allan Freedline, Miami Beach, FL (US)

(73) Assignee: Smith & Nephew, Inc., Memphis, TN (US)

( * ) Notice: Subject to any disclaimer, the term of this patent is extended or adjusted under 35 U.S.C. 154(b) by 326 days.

(21) Appl. No.: 16/720,621

(22) Filed: Dec. 19, 2019

(65) Prior Publication Data

US 2020/0155356 A1 May 21, 2020

Related U.S. Application Data

(63) Continuation of application No. 15/879,382, filed on Jan. 24, 2018, now Pat. No. 10,548,776, which is a continuation of application No. 15/804,780, filed on Nov. 6, 2017, now abandoned, which is a continuation of application No. 14/035,487, filed on Sep. 24, 2013, now Pat. No. 9,820,888, which is a continuation-in-part of application No. 13/202,974, filed as application No. PCT/GB2010/000293 on Feb. 19, 2010, now abandoned, said application No. 14/035,487 is a continuation-in-part of application
(Continued)

(30) Foreign Application Priority Data

Feb. 24, 2009 (GB) ...................................... 0903032

(51) Int. Cl.
*A61F 13/00* (2006.01)

(52) U.S. Cl.
CPC .............................. *A61F 13/00038* (2013.01)

(58) Field of Classification Search
None
See application file for complete search history.

(56) References Cited

U.S. PATENT DOCUMENTS

| 1,975,504 A | 10/1934 | Formhals |
| 2,331,271 A | 10/1943 | Gilchrist |

(Continued)

FOREIGN PATENT DOCUMENTS

| CN | 1293953 A | 5/2001 |
| CN | 2676918 Y | 2/2005 |

(Continued)

OTHER PUBLICATIONS

U.S. Appl. No. 15/804,780, filed Nov. 6, 2017, Greener et al.
(Continued)

*Primary Examiner* — Kim M Lewis
(74) *Attorney, Agent, or Firm* — Knobbe, Martens Olson & Bear, LLP

(57) ABSTRACT

A wound dressing, suitable for use in negative pressure wound therapy, comprising a body of porous material, the body of porous material comprising a plurality of cuts which provide regions of flexibility within the body. Further embodiments relate to methods of manufacturing and method of use of such wound dressings. In addition, the wound dressing can comprise a retaining mechanism removably coupled to the material and configured to retain the material in the expanded conformation.

23 Claims, 17 Drawing Sheets

Related U.S. Application Data

No. 12/443,169, filed as application No. PCT/US2007/079529 on Sep. 26, 2007, now Pat. No. 8,680,360.

(60) Provisional application No. 60/826,922, filed on Sep. 26, 2006.

(56) References Cited

U.S. PATENT DOCUMENTS

| | | | |
|---|---|---|---|
| 2,727,382 A | 12/1955 | Karl et al. | |
| 2,877,765 A | 3/1959 | Bunyan | |
| 2,889,039 A | 6/1959 | Schladermundt et al. | |
| 3,073,304 A | 1/1963 | Schaar | |
| 3,285,245 A | 11/1966 | Eldredge et al. | |
| 3,929,135 A | 12/1975 | Thompson | |
| 3,964,039 A | 6/1976 | Craford et al. | |
| 3,972,328 A | 8/1976 | Chen | |
| 4,029,598 A | 6/1977 | Neisius et al. | |
| 4,093,277 A | 6/1978 | Nolan et al. | |
| 4,095,599 A | 6/1978 | Simonet-Haibe | |
| 4,224,941 A | 9/1980 | Stivala | |
| 4,294,240 A | 10/1981 | Thill | |
| 4,418,691 A | 12/1983 | Yannas et al. | |
| 4,541,426 A | 9/1985 | Webster | |
| 4,624,656 A | 11/1986 | Clark et al. | |
| 4,664,662 A | 5/1987 | Webster | |
| 4,681,562 A | 7/1987 | Beck et al. | |
| 4,690,134 A | 9/1987 | Snyders | |
| 4,699,134 A | 10/1987 | Samuelsen | |
| 4,728,499 A | 3/1988 | Fehder | |
| 4,770,187 A | 9/1988 | Lash et al. | |
| 4,813,942 A | 3/1989 | Alvarez | |
| 4,841,961 A | 6/1989 | Burlage et al. | |
| 4,841,962 A | 6/1989 | Berg et al. | |
| 4,886,697 A | 12/1989 | Perdelwitz, Jr. et al. | |
| 4,929,477 A | 5/1990 | Will | |
| 4,985,467 A | 1/1991 | Kelly et al. | |
| 5,000,172 A | 3/1991 | Ward | |
| 5,000,741 A | 3/1991 | Kalt | |
| 5,010,883 A | 4/1991 | Rawlings et al. | |
| 5,056,510 A | 10/1991 | Gilman | |
| 5,061,258 A | 10/1991 | Martz | |
| 5,080,661 A | 1/1992 | Lavender et al. | |
| 5,106,629 A | 4/1992 | Cartmell et al. | |
| 5,145,906 A | 9/1992 | Chambers et al. | |
| 5,152,757 A | 10/1992 | Eriksson | |
| 5,167,613 A | 12/1992 | Karami et al. | |
| 5,181,905 A | 1/1993 | Flam | |
| 5,238,732 A | 8/1993 | Krishnan | |
| 5,264,218 A * | 11/1993 | Rogozinski | A61L 15/42 424/443 |
| 5,267,952 A | 12/1993 | Gardner | |
| 5,360,420 A | 11/1994 | Cook et al. | |
| 5,397,316 A | 3/1995 | LaVon et al. | |
| 5,415,715 A | 5/1995 | Delage et al. | |
| 5,447,492 A | 9/1995 | Cartmell et al. | |
| 5,489,304 A | 2/1996 | Orgill et al. | |
| 5,501,661 A | 3/1996 | Cartmell et al. | |
| 5,536,264 A | 7/1996 | Hsueh et al. | |
| 5,536,555 A | 7/1996 | Zelazoski et al. | |
| 5,549,584 A | 8/1996 | Gross | |
| 5,562,107 A | 10/1996 | Lavender et al. | |
| 5,591,149 A | 1/1997 | Cree et al. | |
| 5,605,165 A | 2/1997 | Sessions et al. | |
| 5,626,954 A | 5/1997 | Andersen et al. | |
| 5,636,643 A | 6/1997 | Argenta et al. | |
| 5,643,189 A | 7/1997 | Masini | |
| 5,645,081 A | 7/1997 | Argenta et al. | |
| 5,707,499 A | 1/1998 | Joshi et al. | |
| 5,713,881 A | 2/1998 | Rezai et al. | |
| 5,716,411 A | 2/1998 | Orgill et al. | |
| 5,720,714 A | 2/1998 | Penrose | |
| 5,735,145 A | 4/1998 | Pernick | |
| 5,759,570 A | 6/1998 | Arnold | |
| 5,795,439 A | 8/1998 | Euripides et al. | |
| 5,795,584 A | 8/1998 | Totakura et al. | |
| 5,804,021 A | 9/1998 | Abuto et al. | |
| 5,833,646 A | 11/1998 | Masini | |
| 5,852,126 A | 12/1998 | Barnard et al. | |
| 5,868,724 A | 2/1999 | Dierckes, Jr. et al. | |
| 5,960,795 A | 10/1999 | Schultz | |
| 5,968,855 A | 10/1999 | Perdelwitz, Jr. et al. | |
| 5,981,822 A | 11/1999 | Addison | |
| 6,008,429 A | 12/1999 | Ritger | |
| 6,018,092 A | 1/2000 | Dunshee | |
| 6,071,267 A | 6/2000 | Zamierowski | |
| 6,142,982 A | 11/2000 | Hunt et al. | |
| 6,167,613 B1 | 1/2001 | Karami | |
| 6,203,654 B1 | 3/2001 | McFall et al. | |
| 6,207,875 B1 | 3/2001 | Lindqvist et al. | |
| 6,225,523 B1 | 5/2001 | Masini | |
| 6,241,697 B1 | 6/2001 | Augustine | |
| 6,261,283 B1 | 7/2001 | Morgan et al. | |
| 6,297,422 B1 | 10/2001 | Hansen et al. | |
| 6,312,416 B1 | 11/2001 | Brisebois et al. | |
| 6,333,093 B1 | 12/2001 | Burrell et al. | |
| 6,345,623 B1 | 2/2002 | Heaton et al. | |
| 6,398,767 B1 | 6/2002 | Fleischmann | |
| 6,447,799 B1 | 9/2002 | Ullman | |
| 6,478,781 B1 | 11/2002 | Urich et al. | |
| 6,482,491 B1 | 11/2002 | Samuelsen et al. | |
| 6,497,688 B2 | 12/2002 | Lasko | |
| 6,566,575 B1 | 5/2003 | Stickels et al. | |
| 6,599,262 B1 | 7/2003 | Masini | |
| 6,626,891 B2 | 9/2003 | Ohmstede | |
| 6,685,681 B2 | 2/2004 | Lockwood et al. | |
| 6,713,659 B2 | 3/2004 | Bodenschatz et al. | |
| 6,752,794 B2 | 6/2004 | Lockwood et al. | |
| 6,764,462 B2 | 7/2004 | Risk, Jr. et al. | |
| 6,767,334 B1 | 7/2004 | Randolph | |
| 6,770,794 B2 | 8/2004 | Fleischmann | |
| 6,794,554 B2 * | 9/2004 | Sessions | A61F 13/00021 602/43 |
| 6,936,037 B2 | 8/2005 | Bubb et al. | |
| 6,942,628 B1 | 9/2005 | Watson | |
| 6,951,553 B2 | 10/2005 | Bubb et al. | |
| 6,979,324 B2 | 12/2005 | Bybordi et al. | |
| 6,998,511 B2 | 2/2006 | Worthley | |
| 7,004,915 B2 | 2/2006 | Boynton et al. | |
| 7,022,113 B2 | 4/2006 | Lockwood et al. | |
| D525,362 S | 7/2006 | Nielsen et al. | |
| 7,070,584 B2 | 7/2006 | Johnson et al. | |
| 7,108,681 B2 | 9/2006 | Gartstein et al. | |
| 7,108,683 B2 | 9/2006 | Zamierowski | |
| 7,122,712 B2 | 10/2006 | Lutri et al. | |
| D537,948 S | 3/2007 | Smith | |
| 7,216,651 B2 | 5/2007 | Argenta et al. | |
| 7,267,681 B2 | 9/2007 | Dunshee | |
| 7,338,482 B2 | 3/2008 | Lockwood et al. | |
| 7,351,250 B2 | 4/2008 | Zamierowski | |
| 7,361,184 B2 | 4/2008 | Joshi | |
| 7,381,859 B2 | 6/2008 | Hunt et al. | |
| 7,429,689 B2 | 9/2008 | Chen et al. | |
| 7,438,705 B2 | 10/2008 | Karpowicz et al. | |
| 7,468,471 B2 | 12/2008 | Sigurjonsson et al. | |
| 7,485,112 B2 | 2/2009 | Karpowicz et al. | |
| 7,494,482 B2 | 2/2009 | Orgill et al. | |
| 7,534,927 B2 * | 5/2009 | Lockwood | A61F 13/0216 602/46 |
| 7,553,306 B1 | 6/2009 | Hunt et al. | |
| 7,569,742 B2 | 8/2009 | Haggstrom et al. | |
| 7,576,256 B2 | 8/2009 | Björnberg et al. | |
| 7,605,298 B2 | 10/2009 | Bechert et al. | |
| 7,615,036 B2 | 11/2009 | Joshi et al. | |
| 7,622,629 B2 | 11/2009 | Aail | |
| 7,625,362 B2 | 12/2009 | Boehringer et al. | |
| 7,674,948 B2 | 3/2010 | Propp et al. | |
| 7,676,400 B1 | 3/2010 | Dillon | |
| 7,676,784 B2 | 3/2010 | Allen et al. | |
| 7,678,102 B1 | 3/2010 | Heaton | |
| 7,699,823 B2 | 4/2010 | Haggstrom et al. | |
| 7,700,819 B2 | 4/2010 | Ambrosio et al. | |
| 7,708,724 B2 | 5/2010 | Weston | |

(56) References Cited

U.S. PATENT DOCUMENTS

| | | |
|---|---|---|
| 7,718,249 B2 | 5/2010 | Russell et al. |
| 7,722,582 B2 | 5/2010 | Lina et al. |
| 7,749,531 B2 | 7/2010 | Booher |
| 7,753,894 B2 | 7/2010 | Blott et al. |
| 7,754,937 B2 | 7/2010 | Boehringer et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,811,269 B2 | 10/2010 | Boynton et al. |
| 7,815,616 B2 | 10/2010 | Boehringer et al. |
| 7,820,453 B2 | 10/2010 | Heylen et al. |
| 7,838,717 B2 | 11/2010 | Haggstrom et al. |
| 7,846,141 B2 | 12/2010 | Weston |
| 7,857,806 B2 | 12/2010 | Karpowicz et al. |
| 7,896,856 B2 | 3/2011 | Petrosenko et al. |
| 7,909,805 B2 | 3/2011 | Weston |
| 7,910,791 B2 | 3/2011 | Coffey |
| 7,922,703 B2 | 4/2011 | Riesinger |
| 7,942,866 B2 | 5/2011 | Radl et al. |
| 7,951,124 B2 | 5/2011 | Boehringer et al. |
| 7,959,624 B2 | 6/2011 | Riesinger |
| 7,964,766 B2 | 6/2011 | Blott et al. |
| 7,976,519 B2 | 7/2011 | Bubb et al. |
| 7,981,098 B2 | 7/2011 | Boehringer et al. |
| 7,982,087 B2 | 7/2011 | Greener et al. |
| 8,030,534 B2 | 10/2011 | Radl et al. |
| 8,034,037 B2 | 10/2011 | Adams et al. |
| 8,062,272 B2 | 11/2011 | Weston |
| 8,062,331 B2 | 11/2011 | Zamierowski |
| 8,070,773 B2 | 12/2011 | Zamierowski |
| 8,080,702 B2 | 12/2011 | Blott et al. |
| 8,114,126 B2 | 2/2012 | Heaton et al. |
| 8,118,794 B2 | 2/2012 | Weston et al. |
| 8,123,781 B2 | 2/2012 | Zamierowski |
| 8,142,419 B2 | 3/2012 | Heaton et al. |
| 8,172,816 B2 | 5/2012 | Kazala, Jr. et al. |
| 8,187,237 B2 | 5/2012 | Seegert |
| 8,188,331 B2 | 5/2012 | Barta et al. |
| 8,197,467 B2 | 6/2012 | Heaton et al. |
| 8,207,392 B2 | 6/2012 | Haggstrom et al. |
| 8,235,972 B2 | 8/2012 | Adahan |
| 8,246,607 B2 | 8/2012 | Karpowicz et al. |
| 8,273,105 B2 | 9/2012 | Cohen et al. |
| 8,282,611 B2 | 10/2012 | Weston |
| 8,303,552 B2 | 11/2012 | Weston |
| 8,338,402 B2 | 12/2012 | Fry et al. |
| 8,353,931 B2 | 1/2013 | Stopek et al. |
| 8,376,972 B2 | 2/2013 | Fleischmann |
| 8,399,730 B2 | 3/2013 | Kazala, Jr. et al. |
| 8,404,921 B2 | 3/2013 | Lee et al. |
| 8,409,159 B2 | 4/2013 | Hu et al. |
| 8,444,392 B2 | 5/2013 | Turner et al. |
| 8,444,612 B2 | 5/2013 | Patel et al. |
| 8,447,375 B2 | 5/2013 | Shuler |
| 8,460,255 B2 | 6/2013 | Joshi et al. |
| 8,460,257 B2 | 6/2013 | Locke et al. |
| 8,486,032 B2 | 7/2013 | Seegert et al. |
| 8,500,704 B2 | 8/2013 | Boehringer et al. |
| 8,500,776 B2 | 8/2013 | Ebner |
| 8,523,832 B2 | 9/2013 | Seegert |
| 8,535,296 B2 | 9/2013 | Blott et al. |
| 8,540,687 B2 | 9/2013 | Henley et al. |
| 8,545,464 B2 | 10/2013 | Weston |
| 8,545,466 B2 | 10/2013 | Andresen et al. |
| 8,608,776 B2 | 12/2013 | Coward et al. |
| 8,622,981 B2 | 1/2014 | Hartwell et al. |
| 8,628,505 B2 | 1/2014 | Weston |
| 8,632,523 B2 | 1/2014 | Eriksson et al. |
| 8,641,691 B2 | 2/2014 | Fink |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 | 4/2014 | Robinson et al. |
| 8,791,316 B2 | 7/2014 | Greener |
| 8,795,243 B2 | 8/2014 | Weston |
| 8,821,535 B2 | 9/2014 | Greener |
| 8,829,263 B2 | 9/2014 | Haggstrom et al. |
| 8,834,451 B2 | 9/2014 | Blott et al. |
| 8,945,030 B2 | 2/2015 | Weston |
| 8,956,336 B2 | 2/2015 | Haggstrom et al. |
| 9,012,714 B2 | 4/2015 | Fleischmann |
| 9,061,095 B2 | 6/2015 | Adie et al. |
| 9,168,330 B2 | 10/2015 | Joshi et al. |
| 9,220,822 B2 | 12/2015 | Hartwell et al. |
| 9,226,737 B2 | 1/2016 | Dunn |
| 9,302,033 B2 | 4/2016 | Riesinger |
| 9,381,283 B2 | 7/2016 | Adams et al. |
| 9,446,178 B2 | 9/2016 | Blott et al. |
| 9,452,248 B2 | 9/2016 | Blott et al. |
| 9,629,986 B2 | 4/2017 | Patel et al. |
| 9,669,138 B2 | 6/2017 | Joshi et al. |
| 9,770,368 B2 | 9/2017 | Robinson et al. |
| 9,795,725 B2 | 10/2017 | Joshi et al. |
| 9,808,561 B2 | 11/2017 | Adie et al. |
| 9,820,888 B2 | 11/2017 | Greener et al. |
| 10,548,776 B2 | 2/2020 | Greener et al. |
| 11,083,628 B2 | 8/2021 | Greener et al. |
| 2001/0051165 A1 | 12/2001 | Lenz et al. |
| 2002/0035352 A1 | 3/2002 | Ronnberg et al. |
| 2002/0052570 A1 | 5/2002 | Naimer |
| 2002/0062114 A1 | 5/2002 | Murai et al. |
| 2002/0183702 A1 | 12/2002 | Henley et al. |
| 2002/0193721 A1 | 12/2002 | Vandruff |
| 2003/0014025 A1 | 1/2003 | Allen et al. |
| 2003/0014786 P1 | 1/2003 | Meilland |
| 2003/0050590 A1 | 3/2003 | Kirsch |
| 2003/0125646 A1 | 7/2003 | Whitlock |
| 2003/0203011 A1 | 10/2003 | Abuelyaman et al. |
| 2003/0212357 A1 | 11/2003 | Pace |
| 2004/0015115 A1 | 1/2004 | Sinyagin |
| 2004/0019337 A1 | 1/2004 | Moberg-Alehammar et al. |
| 2004/0019338 A1 | 1/2004 | Litvay et al. |
| 2004/0057855 A1 | 3/2004 | Gerlach et al. |
| 2004/0087884 A1 | 5/2004 | Haddock et al. |
| 2004/0167482 A1 | 8/2004 | Watson |
| 2005/0084641 A1 | 4/2005 | Downs et al. |
| 2005/0090860 A1 | 4/2005 | Paprocki |
| 2005/0147656 A1 | 7/2005 | McCarthy et al. |
| 2005/0182445 A1 | 8/2005 | Zamierowski |
| 2005/0215932 A1 | 9/2005 | Sigurjonsson et al. |
| 2005/0222527 A1 | 10/2005 | Miller et al. |
| 2005/0288691 A1 | 12/2005 | Leiboff |
| 2006/0009744 A1 | 1/2006 | Edrman et al. |
| 2006/0020234 A1 | 1/2006 | Chou et al. |
| 2006/0047257 A1* | 3/2006 | Raidel .......... A61F 13/535 604/383 |
| 2006/0161123 A1 | 7/2006 | Kudo et al. |
| 2006/0184150 A1 | 8/2006 | Noel |
| 2007/0010775 A1 | 1/2007 | Lutri |
| 2007/0032763 A1 | 2/2007 | Vogel |
| 2007/0040454 A1 | 2/2007 | Freudenberger et al. |
| 2007/0055029 A1 | 3/2007 | Suzuki et al. |
| 2007/0055209 A1 | 3/2007 | Patel et al. |
| 2007/0060892 A1 | 3/2007 | Propp |
| 2007/0073200 A1 | 3/2007 | Hannigan et al. |
| 2007/0185463 A1 | 8/2007 | Mulligan |
| 2007/0219497 A1 | 9/2007 | Johnson et al. |
| 2007/0219512 A1 | 9/2007 | Heaton et al. |
| 2007/0220692 A1 | 9/2007 | Kusin |
| 2007/0225663 A1 | 9/2007 | Watt et al. |
| 2007/0239232 A1 | 10/2007 | Kurtz et al. |
| 2007/0282309 A1 | 12/2007 | Bengtson et al. |
| 2008/0031748 A1 | 2/2008 | Ihle et al. |
| 2008/0095979 A1 | 4/2008 | Hatanaka et al. |
| 2008/0113143 A1 | 5/2008 | Taylor |
| 2008/0132821 A1 | 6/2008 | Propp et al. |
| 2008/0172017 A1 | 7/2008 | Carlucci et al. |
| 2008/0300555 A1 | 12/2008 | Olson et al. |
| 2008/0306456 A1 | 12/2008 | Riesinger |
| 2009/0012483 A1 | 1/2009 | Blott et al. |
| 2009/0043268 A1 | 2/2009 | Eddy et al. |
| 2009/0093550 A1 | 4/2009 | Rolfes et al. |
| 2009/0099519 A1 | 4/2009 | Kaplan |

(56) References Cited

U.S. PATENT DOCUMENTS

| | | |
|---|---|---|
| 2009/0105670 A1 | 4/2009 | Bentley et al. |
| 2009/0105671 A1 | 4/2009 | Daggar et al. |
| 2009/0137973 A1 | 5/2009 | Karpowicz et al. |
| 2009/0227969 A1 | 9/2009 | Jaeb et al. |
| 2009/0306609 A1 | 12/2009 | Blott et al. |
| 2009/0326430 A1 | 12/2009 | Frederiksen et al. |
| 2010/0010462 A1 | 1/2010 | Kurata |
| 2010/0022990 A1 | 1/2010 | Karpowicz et al. |
| 2010/0063484 A1 | 3/2010 | Heagle |
| 2010/0106184 A1 | 4/2010 | Coward et al. |
| 2010/0160874 A1 | 6/2010 | Robinson et al. |
| 2010/0179515 A1 | 7/2010 | Swain et al. |
| 2010/0196106 A1 | 8/2010 | Allen |
| 2010/0198127 A1* | 8/2010 | Addison ........... A61F 13/00995 602/48 |
| 2010/0249733 A9 | 9/2010 | Blott et al. |
| 2010/0312159 A1 | 12/2010 | Aali et al. |
| 2011/0021964 A1 | 1/2011 | Larsen et al. |
| 2011/0054283 A1 | 3/2011 | Shuler |
| 2011/0066096 A1 | 3/2011 | Svedman |
| 2011/0077605 A1 | 3/2011 | Karpowicz et al. |
| 2011/0112492 A1 | 5/2011 | Bharti et al. |
| 2011/0118683 A1 | 5/2011 | Weston |
| 2011/0224631 A1 | 9/2011 | Simmons |
| 2011/0282310 A1 | 11/2011 | Boehringer et al. |
| 2011/0313373 A1 | 12/2011 | Riesinger |
| 2011/0313374 A1 | 12/2011 | Lockwood et al. |
| 2012/0041402 A1 | 2/2012 | Greener |
| 2012/0059412 A1 | 3/2012 | Fleischmann |
| 2012/0143113 A1 | 6/2012 | Robinson et al. |
| 2012/0144989 A1 | 6/2012 | De Plessis et al. |
| 2012/0150133 A1 | 6/2012 | Heaton et al. |
| 2012/0172926 A1 | 7/2012 | Hotter |
| 2012/0191054 A1 | 7/2012 | Kazala, Jr. et al. |
| 2012/0209226 A1 | 8/2012 | Simmons et al. |
| 2013/0131564 A1 | 5/2013 | Locke et al. |
| 2013/0138054 A1 | 5/2013 | Fleischmann |
| 2013/0197457 A1 | 8/2013 | Kazala et al. |
| 2013/0253401 A1 | 9/2013 | Locke et al. |
| 2013/0274688 A1 | 10/2013 | Weston |
| 2013/0310781 A1 | 11/2013 | Phillips et al. |
| 2014/0068914 A1 | 3/2014 | Coward et al. |
| 2014/0180225 A1 | 6/2014 | Dunn |
| 2015/0065965 A1 | 3/2015 | Haggstrom et al. |
| 2015/0112311 A1 | 4/2015 | Hammond et al. |
| 2015/0148760 A1 | 5/2015 | Dodd et al. |
| 2015/0150729 A1 | 6/2015 | Dagger et al. |
| 2015/0159066 A1 | 6/2015 | Hartwell et al. |
| 2015/0196431 A1 | 7/2015 | Dunn |
| 2015/0209492 A1 | 7/2015 | Blott et al. |
| 2017/0290709 A1 | 10/2017 | Adie et al. |
| 2018/0147091 A1 | 5/2018 | Greener et al. |
| 2021/0386592 A1 | 12/2021 | Greener et al. |

FOREIGN PATENT DOCUMENTS

| | | |
|---|---|---|
| CN | 2843399 Y | 12/2006 |
| CN | 101415818 A | 4/2009 |
| DE | 34 43 101 | 5/1986 |
| DE | 4030465 A1 | 4/1992 |
| DE | 20 2004 017 052 | 7/2005 |
| DE | 10 2005 007016 | 8/2006 |
| DE | 102011002268 A1 | 10/2012 |
| EP | 0053936 A2 | 6/1982 |
| EP | 0 340 018 | 11/1989 |
| EP | 0768071 A1 | 4/1997 |
| EP | 1 320 342 | 6/2003 |
| EP | 1353001 A1 | 10/2003 |
| EP | 0630629 B1 | 11/2004 |
| EP | 1 614 789 | 1/2006 |
| EP | 1 476 217 | 3/2008 |
| EP | 1 955 887 | 8/2008 |
| EP | 2 279 016 | 2/2011 |
| EP | 2 366 721 | 9/2011 |
| EP | 2 462 908 | 6/2012 |
| EP | 2 341 955 | 12/2012 |
| EP | 2 563 421 | 3/2013 |
| EP | 2 567 717 | 3/2013 |
| EP | 2 594 299 | 5/2013 |
| EP | 2 601 984 | 6/2013 |
| EP | 2 623 137 | 8/2013 |
| EP | 2 367 517 | 9/2013 |
| EP | 2 544 642 | 1/2015 |
| EP | 2269603 B1 | 5/2015 |
| EP | 2 931 197 | 10/2015 |
| EP | 3 085 344 | 10/2016 |
| EP | 3 139 878 | 3/2017 |
| FR | 1 163 907 | 10/1958 |
| GB | 821959 | 10/1959 |
| GB | 1224009 | 3/1971 |
| GB | 1255395 | 12/1971 |
| GB | 2195255 | 4/1988 |
| GB | 2331937 A | 6/1999 |
| GB | 2389794 A | 12/2003 |
| JP | S5230463 U | 3/1977 |
| JP | S57119738 A | 7/1982 |
| JP | H02-139624 | 11/1990 |
| JP | H02-139625 | 11/1990 |
| JP | H02131432 U | 11/1990 |
| JP | H06-339495 | 12/1994 |
| JP | H07231909 A | 9/1995 |
| JP | H11-056900 | 3/1999 |
| JP | 2004-000465 | 1/2004 |
| JP | 2006025918 A | 2/2006 |
| JP | 2008073187 A | 4/2008 |
| JP | 2008183244 A | 8/2008 |
| RU | 62504 U1 | 4/2007 |
| WO | WO 1983/00742 | 3/1983 |
| WO | WO 1990/010424 | 9/1990 |
| WO | WO 1992/010983 | 7/1992 |
| WO | WO 1995/014451 | 6/1995 |
| WO | WO 1996/001731 | 1/1996 |
| WO | WO 1996/005873 | 2/1996 |
| WO | WO 1997/11658 | 4/1997 |
| WO | WO-9741816 A1 | 11/1997 |
| WO | WO-9963922 A1 | 12/1999 |
| WO | WO-0154743 A1 | 8/2001 |
| WO | WO 2002/092783 | 11/2002 |
| WO | WO-03051409 A1 | 6/2003 |
| WO | WO 2003/072748 | 9/2003 |
| WO | WO-03086232 A2 | 10/2003 |
| WO | WO 2004/077387 | 9/2004 |
| WO | WO-2005009488 A2 | 2/2005 |
| WO | WO 2005/025447 | 3/2005 |
| WO | WO 2005/123170 | 12/2005 |
| WO | WO 2006/052839 | 5/2006 |
| WO | WO 2006/087021 | 8/2006 |
| WO | WO 2006/099137 | 9/2006 |
| WO | WO-2007013049 A1 | 2/2007 |
| WO | WO-2007066699 A1 | 6/2007 |
| WO | WO 2008/039223 | 4/2008 |
| WO | WO 2008/039839 | 4/2008 |
| WO | WO 2008/064502 | 6/2008 |
| WO | WO-2008100437 A1 | 8/2008 |
| WO | WO 2008/104609 | 9/2008 |
| WO | WO 2008/141228 | 11/2008 |
| WO | WO-2009001590 A1 | 12/2008 |
| WO | WO 2009/021523 | 2/2009 |
| WO | WO 2009/112848 | 9/2009 |
| WO | WO 2009/158131 | 12/2009 |
| WO | WO 2010/097570 | 9/2010 |
| WO | WO 2010/147535 | 12/2010 |
| WO | WO 2011/137230 | 11/2011 |
| WO | WO 2012/021553 | 2/2012 |
| WO | WO 2012/082716 | 6/2012 |
| WO | WO 2012/082876 | 6/2012 |
| WO | WO 2012/106590 | 8/2012 |
| WO | WO 2012/112204 | 8/2012 |
| WO | WO 2012/136707 | 10/2012 |
| WO | WO 2013/012381 | 1/2013 |
| WO | WO 2013/074829 | 5/2013 |
| WO | WO 2013/136181 | 9/2013 |
| WO | WO 2013/175309 | 11/2013 |

(56) References Cited

FOREIGN PATENT DOCUMENTS

| WO | WO 2013/175310 | 11/2013 |
| WO | WO 2014/013348 | 1/2014 |
| WO | WO 2014/014842 | 1/2014 |
| WO | WO 2014/014871 | 1/2014 |
| WO | WO 2014/014922 | 1/2014 |
| WO | WO 2014/165275 | 10/2014 |
| WO | WO 2015/172108 | 11/2015 |
| WO | WO-2016169948 A1 | 10/2016 |

OTHER PUBLICATIONS

U.S. Appl. No. 15/850,996, filed Dec. 21, 2017, Hartwell.
"Technology Watch", May 1989, in 1 page.
Alexander, J. et al., "Clinical Evaluation of Epigard, A New Synthetic Substitute for Homograft and Heterograft Skin", The Journal of Trauma, vol. 13, No. 4, Apr. 1973, pp. 374-383, in 10 pages.
Applications for Modification to HCPCS Level II Code Set in the 2005-2006 Coding Cycle, in 60 pages. URL: www.cms.hhs.gov/medicare/hcpcs/.
Blumberg, J. et al., The Effect of Specific Compression on Soft-Tissue Response to Formalinized PVA (Ivalon) Sponge: A Critical Evaluation, Annals Surg., Mar. 1960, vol. 151(3), pp. 409-418, in 10 pages.
Boland, E.D. et al. "Utilizing acid pre-treatment and electrospinning to improve biocompatibility poly(glycolic acid) for tissue engineering", J. Biomed. Mater. Res. Part B: Appl Biomater 71B 144-152, 2004, in 9 pages.
Boland, E.D. et al., "Tailoring Tissue Engineering Scaffolds Using Electrostatic Processing Techniques: A Study of Poly(Glycolic Acid) Electrospinning", Journal of Macromolecular Science A. Pure and Applied Chemistry, A38(12), pp. 1231-1243 (2001), in 13 pages.
Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.
Hougaard, H. et al., "The open abdomen: temporary closure with a modified negative pressure therapy technique," International Wound Journal, 2014, pp. 13-16, ISSN 1742-4801, in 4 pages.
International Preliminary Report on Patentability, re PCT Application No. PCT/US2007/079529, dated Jan. 5, 2010.
International Search Report, re PCT Application No. PCT/US2007/079529, dated Mar. 19, 2008, as listed in the revised version of WO 2008/039839 A3, in 6 pages.
International Search Report, re PCT Application No. PCT/GB2010/000293, dated May 27, 2010.
International Preliminary Report on Patentability, re PCT Application PCT/GB2010/000293, dated Aug. 30, 2011.
Kendall ULTEC Hydrocolloid Dressing (4"×4"), product ordering page, web page downloaded Jul. 13, 2014, in 1 page.
Ma, P., "Scaffolds for tissue fabrication", Materials Today, Review, May 2004, in 11 pages.
Advantec MFS, Inc., "Membrane Filters" (catalog), accessed Jan. 29, 2016 (publication date unknown, but believed to be copyright 2001-2011), in 17 pages. URL: http://www.advantecmfs.com/catalog/filt/membrane.pdf#page=11.
Middleton, J. et al., "Synthetic biodegradable polymers as medical devices" (HTML), Medical Plastics and Biomaterials Magazine, Mar. 1998, in 14 pages.
Protz, K., "Moderne Wundauflagen unterstutzen Heilungsprozess", Wundversorgung: Indikation und Anwendung, Geriatrie Journal, Apr. 2005, pp. 3333-3339, with translation, in 17 pages.
Smith & Nephew, "PICO Single Use Negative Pressure Wound Therapy System", spiral booklet, Mar. 2011, in 7 pages.
Stewart, J., "World Wide Wounds—Next Generation of Products for Wound Management", 2002, in 13 pages.
U.S. Appl. No. 12/443,169, Lattice Dressing, filed Nov. 17, 2009.
U.S. Appl. No. 13/202,974, Drapeable Wound Dressing, filed Oct. 5, 2011.
Written Opinion for Application No. PCT/GB2010/000293, dated May 27, 2010, 6 pages.
Written Opinion for Application No. PCT/US2007/079529, dated Mar. 19, 2009, 14 pages.
Personally Delivered, "Polyskin Transparent Film Dressing", Retrieved from the Internet URL: https://www.personallydelivered.com/6640-polyskin-transparent-film-dressing, on Mar. 4, 2022, 4 pages.
Wikipedia, "Parallel (geometry)," retrieved from https://en.wikipedia.org/w/index.php?title=Parallel_(geometry)&oldid=1080576469, last edited on Apr. 2, 2022, 9 pages.

* cited by examiner

WOUND DRESSING

CROSS-REFERENCE TO RELATED APPLICATIONS

This application is a continuation of U.S. patent application Ser. No. 15/879,382, filed Jan. 24, 2018, which is a continuation of abandoned U.S. patent application Ser. No. 15/804,780, filed Nov. 6, 2017, which is a continuation of U.S. patent application Ser. No. 14/035,487, filed Sep. 24, 2013 and now U.S. Pat. No. 9,820,888, which is a continuation in part of U.S. patent application Ser. No. 12/443,169, filed Nov. 17, 2009 and now U.S. Pat. No. 8,680,360, entitled LATTICE DRESSING, which is a National Phase Application of PCT Patent Application No. PCT/US2007/079529 filed Sep. 26, 2007, entitled LATTICE DRESSING, which claims priority to U.S. Provisional Application No. 60/826,922, filed Sep. 26, 2006, entitled LATTICE DRESSING. This application is also a continuation-in-part of U.S. Patent Application No. 13/202,974, filed Oct. 5, 2011, entitled DRAPEABLE WOUND DRESSING, which is a National Phase Application of PCT Patent Application PCT/GB2010/000293, filed Feb. 19, 2010, entitled DRAPEABLE WOUND DRESSING, which claims priority to Great Britain Application No. 0903032.1, filed Feb. 24, 2009, entitled DRAPEABLE WOUND DRESSING. The contents of the aforementioned applications are hereby incorporated by reference in their entireties as if fully set forth herein. The benefit of priority to the foregoing applications is claimed under the appropriate legal basis, including, without limitation, under 35 U.S.C. § 119(e).

BACKGROUND OF THE INVENTION

Field of the Invention

This application describes embodiments of apparatuses, methods, materials, methods of manufacture, and systems for the treatment of wounds, specifically to aid in packing and treating wounds.

This application further relates to improved wound dressing materials. In particular this application relates to wound dressing materials with improved drapeability, which allows them to more easily conform to the shape of a surface over which they are placed. Especially, but not exclusively, the present application relates to foam materials, especially those suitable for use in negative pressure wound therapy (NPWT).

Description of the Related Art

Wound dressings are commonly manufactured from sheet materials. These materials include transparent films and adhesives and opaque foams and fibres. These materials generally retain their transparency or opacity upon fluid absorption, the exception being carboxymethylcellulose-based hydrofibre (which is initially opaque and becomes transparent when wet). Wound dressings which rely upon a foam element for exudate management are opaque and require removal and exchange for a new dressing during every wound inspection. This is a disadvantage of opaque dressings, for example, including a foam element. Foam-based dressings also have limited extensibility due to the mechanical properties inherent in a material of foam structure; this can cause problems when attempting to dress locations of high curvature. In spite of these performance disadvantages, the use of foam-based wound dressings or dressing elements dominates woundcare. This may be due to their excellent absorbency, low dry weight, cut-ability and mouldability. Limited extensibility is not restricted to foams; this is also a property of the films commonly applied in medical devices.

The single-axis lattice cutting of monolithic materials, including the sheet materials utilised in wound dressings has been disclosed in (GB821,959). However, once cut, these materials are not extended in any manner until post-application to the wound, and only then as a result of the flexing of the limb or other part of the body on which the dressing is worn. Whilst this type of dressing does enable some ease of movement for the patient, the material only permits minimal visibility of the wound. Additionally, the size of apertures and thus the permeability of the material, particularly important for the release of exudates from the wound, cannot be controlled.

There is a need for a wound dressing which can be established in an extended conformation both prior to application and during application to a wound.

There is a need for a wound dressing which can be retained within a defined extended conformation both prior to application and during application to a wound.

There is a need for a wound dressing which allows visualisation of the wound immediately upon application of the dressing.

There is a need for a wound dressing which has a controlled aperture profile, which enables control of exudate egress.

There is a need for a wound dressing which has a controlled contractile profile for promoting wound closure.

NPWT is a relatively new treatment for open wounds. Typically in NPWT the wound cavity or surface is filled or covered with a material that allows the transmission of a partial vacuum (i.e. does not completely collapse) to the wound bed when a negative pressure is applied to the wound area, and also allows fluids to pass from the wound bed towards the source of negative pressure. There are two primary approaches to NPWT, gauze or foam types. The gauze type (also referred to as the Chariker-Jeter technique) involves the use of a drain wrapped in gauze topped by a sealed dressing. The foam type involves the use of foam placed over or in the wound. The present invention is directed primarily, but not exclusively, towards the foam type of NPWT.

In foam based NPWT the wound is filled or covered with a porous, compressible foam packing material and covered over and sealed with flexible sheet (a drape) that is fairly impermeable to fluids. A tube is inserted under or through the drape into the wound site and its distal end is connected to a vacuum source (commonly a pump). The wound cavity, enclosed by the drape and tissue, contracts under the force of atmospheric pressure and compresses the packing material visibly. Gross tissue movement ceases after a few tens of seconds and fluid flow from the wound (withdrawn from the tissue) ensues. The fluid is transmitted through the packing material and up the vacuum tube to a collection receptacle positioned between the distal end of the tube and the vacuum source. The material mechanically supports the tissue to which it is applied, and also allows the free flow of fluids away from the site when a vacuum is applied, even when compressed. A good material for this application is hydrophobic, reticulated polyurethane foam of very high free internal volume. However, articles of high free internal volume tend to be poorly drapeable due to the requirement for their structure to mechanically support their high free internal volume, and this is the case in current foams applied in NPWT.

The foams, which in other regards are near optimal for NPWT, are very poorly conformable to the site of application especially prior to the application of a covering drape and vacuum being applied. This is true for cavity wounds of concave geometry, and surface wounds, e.g. to the extremities, of convex geometry.

Monolithic articles of high free internal volume are able to support their own external dimensions by virtue of their mechanical properties, i.e. they are relatively stiff. This factor has the side effect of making such solid objects poorly drapeable and this is not desirable for all applications. For some applications, the mechanical integrity of the structure is not required at the scale of the monolith itself For medical applications involving the application of articles to the body, both good drapeability and good resistance to compression under loading are desirable attributes.

SUMMARY OF THE INVENTION

The visibility through an opaque material can be increased by the creation of apertures through it. However, the creation of apertures, for example by hole-punching, has the disadvantages of resulting in the generation of waste and also the mechanical weakening of the material. By forming through slits in a material, these slits being capable of expanding to form apertures on extension of the material, we have been able to achieve both increased visibility of the wound and increased extensibility of the material, without significant material waste. In this manner, it is also possible to achieve extension of the slit to form a circular hole without mechanically weakening the material.

Therefore, according to an aspect of the invention there is provided a lattice comprising a material having at least one slit, the slit being capable of expansion into an aperture, the lattice having i) a first conformation, wherein the slit is substantially closed, and ii) a second conformation, wherein the lattice is stretched by the application of an extensive force expanding the slit to form an aperture having a first dimension.

Material having a slit or plurality of slits is referred to as a lattice, and prior to extension of the material, the lattice is referred to as being in a "first conformation" or "initial conformation" or "closed lattice conformation" wherein the slits are substantially closed. A substantially closed slit is a slit which has a conformation that allows no or substantially no visual inspection of the wound through the lattice with the naked eye.

Preferably, the material is a polyurethane foam or a silicone elastomer, for example.

The cutting of a largely two-dimensional or flat material and a three-dimensional material to form slits can be achieved by any means known in the art, for example laser cutting or blade pressing. The cutting method can be a batch process or continuous process. The cutting arrangements of two-dimensional material are preferably two-dimensional and along the x and y plane. The cutting arrangements of three-dimensional material are preferably three-dimensional and along the x, y and z planes.

The material may be cut so that the slits form a parallel, staggered, patterned or random arrangement.

Cuts are not restricted to any particular geometry; they may be straight-edged or curved. Straight-edged cuts include uni-directional arrangements, where all cuts are parallel, and multi-directional arrangements, where all cuts are non-parallel. Curved-cuts include arrangements radiating in an outwardly direction from a central point of the material and describing a circumference of a circle.

Generally speaking, the greater the number of cuts and thus excise of material, the more flexible and extensible will be the lattice formed from the material. However, the geometry of the cutting arrangement will also alter the mechanical properties of the material. Each different cutting geometry will provide a lattice having somewhat different mechanical properties and thus provide lattices of different flexibility and extensibility.

When cutting slits into the material to form the lattice, it is preferable that a minimum amount of material is removed. This avoids the detrimental effect on the structural integrity, and more particularly the mechanical strength of the lattice formed, which would otherwise happen where a larger amount of material was removed as in the case of the prior art where material is removed to form holes.

Preferably, the amount of material removed to form the lattice is therefore, for example, less than about 50% of the initial material volume, more preferably less than about 10% of the initial material volume, and ideally, less than about 1% of the initial material volume. Preferably, the excise of material to form the lattice gives rise to no or substantially no visual removal of material.

When the slits have been formed by cutting the material, the surface area of the resulting lattice can be extended, to about 25%-75% greater than the surface area of the original material. Extension of the lattice opens the slits forming a plurality of apertures/structural voids of a first dimension. The lattice in this extended form is referred to as an open lattice or having an "open lattice conformation", "second conformation" or "extended conformation".

The open lattice is established by an extensive force prior to or immediately prior to and during attachment to the site of application, for example, a wound site.

The lattice has a top or non-wound contacting surface and a bottom or wound contacting surface. The open lattice can be made from any suitable extendible material, for example, polyurethane foam.

The extensive force can be applied to the lattice in a unidirectional, bidirectional or isotropical manner and can be achieved by any means known to the skilled artisan, for example by drawing between rollers running at differential speeds. A process of extending the material in a controlled manner is considered particularly advantageous as this allows apertures/structural voids of predetermined dimensions and of particular interest to be formed.

Preferably, the lattice is extended to 25-75% of its maximum geometrical extension limit. The maximum geometrical extension limit is defined as the point at which the rate of change of the open volume or area of the apertures is zero or substantially zero. More preferably, the lattice is extended to maximise the open volume or area of the apertures, which may not necessarily be related to the maximum geometric extension.

Preferably, once the lattice has been extended into its second conformation, it can be retained in this conformation by the use of a retaining means. The retaining means may be adhered to a surface of the open lattice in any conventional manner. The retaining means can be a physical entity, such as a structural element, for example.

In an embodiment of the invention, the structural element can be a mechanically stiff backing layer, for example, the backing layer being stiff enough to maintain the extended open lattice conformation prior to and during application of the lattice to the wound site. The backing layer may comprise any suitable material, but is preferably plastic or paper.

Additionally, the backing layer is easily releasable from the material. The release of the backing layer may be facilitated by a release tab or gripping portion associated with the backing layer.

The backing layer can be applied directly or indirectly to the open lattice, thus retaining and supporting it in the extended, or second or open lattice conformation prior to and during application. The backing layer has a sufficient mechanical stiffness to resist the inherent contractile force of the open lattice when the extensive force is removed, thereby retaining the lattice in the extended or open lattice conformation. Once the open lattice has been applied to the wound site the backing layer is removed. On removal of the backing layer, the contractile force is transferred to the wound site promoting closure of the wound. Removal of the backing layer also causes the surface area of the lattice and the volume of the voids established therein by the extensive force to shrink.

The extensive force applied to the lattice to form the open lattice is translated into a contractile force when the extensive force is removed. In embodiments of the invention more than about 10% of the extensive force is translated to a contractile force upon removal of the retaining means. In preferred embodiments of the invention more than about 50% of the extensive force is translated to a contractile force upon removal of the retaining means.

In this manner, a contractile force can be applied to the site of application. The use of such a lattice at a wound site, either directly or indirectly (for example, as part of a wound dressing) has the advantage of promoting wound closure, as a result of the contractile forces pulling the edges of the wound together.

By controlling the lattice and open lattice geometry (both the cut and the orientation of extension), it is possibly to control the geometry of the contractile force.

Upon removal of the retaining means, the open lattice preferably recovers more than 1% of the difference between its dimensions prior to extension and those same dimensions post-extension. More preferably, the open lattice recovers more than about 5% of the difference, and ideally recovers more than 10% of the difference.

In this embodiment of the invention, the greater the extension of the lattice the greater will be the contractile force on removal of the backing layer.

The invention is also concerned with the application of the open lattice both internally and externally of the body and on normal or injured tissue such that, following application of the open lattice, the extensive force can be released and transmitted to the attached tissue as a compressive force.

For the contraction of linear wounds, for example post-operative surgical incisions, lattices extensible along a single axis are preferred, as these lattices will impart contraction along a single axis, which when the lattice is appropriately position on the wound will be directed perpendicular to the line of the incision. For the contraction of two-dimensional wounds, for example chronic wounds such as pressure ulcers, lattices extensible along multiple axes are preferred.

Preferably, the lattice is extensible in a mechanically isotropic manner, enabling wound contraction to be directed towards the centre of the wound.

Alternative embodiments provide for the backing layer to be fixed to the non-wound contact surface of the open lattice. In this case the backing layer is a transparent material so that visual inspection of the wound is possible through the apertures of the lattice. It will be appreciated that in this embodiment, no contractile force is applied to the wound from the open lattice.

In another embodiment of the invention, the lattice can be of a material which allows it to also function as the retaining means. For example, the lattice can be made from so-called SMART materials (also referred to as shape-memory materials). The shape of SMART materials can be altered in a controlled fashion by external stimuli, such as stress, temperature, moisture, pH, electric or magnetic fields. In embodiments of the invention, the material is a SMART material. The lattice formed from the SMART material is extended into and retained in the second or open lattice conformation by the application of one or more external stimuli. Post-application of the open lattice to a wound site, further controlled exposure of the open lattice to an external stimulus would result in the open lattice fully or partially contracting to its original, "remembered" dimensions or first conformation. In a wound site, the open lattice could also be initiated or encouraged to contract by exposure to the moisture content of a wound exudate.

In another embodiment of the invention, the structural element can be a transparent film, for example a polyurethane film, fixedly or removably applied to the non-wound contact surface of the open lattice or to the non-wound contact surface and wound contact surface of the open lattice. The film is not as structurally rigid or stiff as the backing layer so that it can not hold the open lattice in a sufficiently extended form to provide a contractile force to promote closure of the wound if removed. Instead, the film keeps a more relaxed open conformation so that the slits remain apertures to allow visual inspection of the wound. The film of this embodiment also acts as a bacterial barrier which is particularly important when the lattice is administered to external wounds.

In further embodiments, both the film and backing layer may be used. The backing layer forms the external non-wound contacting surface and may be removable or fixed.

In yet a further embodiment, the lattice can be extended by hand. Gripping portions or tabs maybe provide at a periphery of the material to give the hand purchase, for example, aiding extension of the lattice by hand. The gripping tabs can be located to allow a more effective extension of the lattice and formation of apertures or structural voids from the slits. Once the lattice has been applied to the wound site the gripping portions are released. On release of the gripping portions, the contractile force of the open lattice is transferred to the wound site promoting closure of the wound. Release of the gripping portions also causes the surface area of the open lattice and the volume of the voids established therein, by the extensive force, to shrink. After the lattice has been secured to the wound site, the gripping portions can be removed from the lattice by cutting, for example. This will prevent the free ends of the gripping portions from snagging. Preferably, the lattice also has a polyeurethane film attached to both the wound and non-wound contact surfaces of the lattice. The polyurethane film will extend with the lattice to form an open lattice and will also act as a bacterial barrier.

In embodiments of the invention the lattice is a wound dressing. In alternative embodiments of the invention the lattice can form a part (for example a layer) of a wound dressing.

In an example of the lattice being incorporated into a wound dressing, a moisture permeable top-film can be applied to the non-wound contacting surface of the lattice (for example, by heat lamination), and the removable backing layer applied to the top-film. The top film can be a polyurethane film, for example. Optionally, a perforated layer of polyurethane film can be applied to the wound contact surface of the polyurethane foam lattice. The polyurethane film applied in this way will prevent the polyurethane foam sticking to the wound which may otherwise occur.

Therefore, according to a further aspect of the invention there is provided a wound dressing consisting of or comprising the lattice of the invention.

In an embodiment of this aspect of the invention the lattice material is a polyurethane foam and the retaining means is a backing sheet adhered temporarily to a non wound contacting surface of the lattice (for example, by a suitable adhesive or surface energy). The backing sheet is of a plastic material (for example, a polymeric film) or paper material (for example, reinforced paper or cardboard). The backing sheet is removed from the open lattice once the wound dressing has been applied to the wound by any suitable means known in the art, for example, by adhesive, sutures, staples or topical pressure.

Preferably, the material is sufficiently elastic to allow a return, unaided or unhindered, of the open lattice to the first conformation, wherein the slits are substantially closed, after being stretched, deformed, compressed, or expanded. Materials conventionally utilised in wound dressings, such as foams (for example, polyurethane foam), silicone-based material (for example, a silicone elastomer), hydrofibre, films, non-woven and woven materials, demonstrate such elastic properties and are suitable materials.

Such elasticity results in the material exerting a spring-like contractile force following the removal of the extensive force, for example, by the removal of the retaining means. This contractile force results in the open lattice forming a "third conformation" or "contracted conformation", in which the apertures/structural voids are contracted to a smaller, second dimension.

In embodiments of the invention the material is a monolith.

According to a further aspect of the invention there is provided a wound dressing comprising a material having;
  i) an initial conformation,
  ii) an expanded conformation resulting from the application of an extensive force to the material, wherein the removal of the extensive force causes a contraction of the material, and
  iii) the wound dressing including means for retaining the material in the expanded conformation.

The material of this aspect of the invention is sufficiently expandable and contractible (partially or fully) from and to an initial conformation, without the requirement for the provision of slits. For example, the material can have elastic properties which closely resemble, for example, LYCRA® (Invista, US).

In an embodiment of this aspect of the invention, the material is provided with at least one slit and preferably with a plurality of slits.

According to a further aspect of the invention there is provided a method of promoting the closure of a wound, the method comprising the steps of;
  a) providing a material having a at least one slit to form a lattice, the slit being capable of expansion into an aperture, the lattice having:
    i) a first conformation, wherein the slit is substantially closed, and,
    ii) a second conformation, wherein the slit is expanded into an aperture having a first dimension,
    iii) retaining the lattice in the second conformation prior to application to a wound site,
    iv) applying the lattice in its second conformation to the wound site, and, optionally,
  c) allowing the lattice to retract from the second conformation towards the first conformation after application to the wound site.

In embodiments of the invention the open lattice can be applied directly to a wound. In alternative embodiments of the invention the open lattice can form a part (for example a layer) of a wound dressing which is applied to a wound.

The invention is particularly suited for application to topical and internal wounds, for example traumatic injuries, surgical incision wounds and open chronic wounds. Surgical wounds include those that are the result of plastics or maxillofacial operations, mastectomy or caesarean section.

The direction of the contractile force is influenced by the geometry of cut in the material to form the lattice, the geometry of extension of the lattice and the geometry of the attachment points between the lattice or wound dressing and the tissue.

The open lattice or wound dressing can be applied to the wound site using any suitable technique and attachment means known in the art, for example, adhesive, sutures, staples or topical pressure. Topical pressure can be provided by compression bandaging or atmospheric pressure acting upon a cavity of reduced pressure relative to the external atmosphere. Attachment can be achieved at specific locations on the open lattice or wound dressing or may cover the entire surface thereof. For topical applications, attachment is preferably achieved by an area exceeding 50% of the total area of the open lattice or wound dressing in contact with the site of application. More preferably, for topical applications, attachment is achieved by a pressure sensitive adhesive, for example an acrylate-based adhesive. Typically, the adhesive forms a layer on the wound contact surface of the open lattice or wound dressing.

According to a further aspect of the invention there is provided a method of manufacturing a wound dressing comprising the steps of,
  (a) providing a first material,
  (b) establishing the material in an extended conformation by applying an extensive force to at least part of the material, and
  (c) retaining the material in the extended conformation by use of a retaining means.

Preferably, the method of manufacture includes the step of forming at least one slit and more preferably a plurality of slits in the material to form a lattice. According to yet a further aspect of the invention there is provided a method of manufacturing a wound dressing comprising the steps of,
  (a) providing a first material, and
  (b) forming at least one slit in said first material to form a lattice.

Preferably, the method of manufacture includes the steps of,
  (a) applying an extensive force to at least part of the lattice to establish the lattice in an extended or open conformation, and
  (b) retaining the lattice in the extended or open conformation by use of a retaining means.

Examples of materials for use as the first material, include foams, such as polyurethane foam and silicone-based elastomers.

An example of a suitable material for use as the retaining means is a polymeric film, such as polyurethane film. Other suitable materials include polyester, polyethylene and polypropylene which can be perforated or extruded net.

In some embodiments, there is provided a wound dressing comprising a body of porous material, the body of porous material comprising a plurality of cuts which provide regions of flexibility within the body.

While the plurality of cuts provide regions of flexibility within the body, they are not capable of rendering portions of the body frangible, such that the portions are relatively easily severable from the body.

Preferably the porous material is a wound packing foam suitable for use in negative pressure wound therapy (NPWT). Particularly suitable foams for NPWT include polyurethane foam, typically reticulated polyurethane foam of very high free internal volume, e.g. 80% or higher, preferably 90% or higher free internal volume. Typical foams used in NPWT have porosities in the range 30-60 ppi (pores per inch) and mean pore diameters in the range 300-800 μm. However, other suitable foams are known in the art and may be equally employed. In general suitable foams have an open porous structure, to allow transmission of the negative pressure to the wound bed, and sufficient mechanical strength to prevent the negative pressure (typically approximately 80-125 mm Hg below ambient atmospheric pressure) from collapsing the structure of the foam.

Suitably the cuts are slits. Herein this section and elsewhere in this specification, the term slit is intended to mean a cut which is generally long and thin, and preferably straight and linear. In practice, slits in foam are typically effectively 2-dimensional as the resilience of the foam means that the slit is essentially closed unless the material is stretched. Suitably the slits are from 10 mm to 70 mm in length, preferably from 20 mm to 50 mm, especially from 25 mm to 40 mm. Slits of around 30 mm have been found to be particularly effective in a typical NPWT, though there is of course scope to vary this.

Providing cuts, e.g. slits, confers macroscopic flexibility, while not substantially affecting the microscopic mechanical properties of the body, i.e. to resist compression under negative pressure. This flexibility allows the body of porous material to drape more easily, i.e. to conform to the shape of the wound to be dressed.

In a preferred embodiment, the body comprises at least one linear series of slits, each slit being separated from an adjacent slit by a gap. By "linear series of slits" it is intended to mean a plurality of generally linear slits, each slit generally aligned along a straight line in a series, with a gap separating each slit from adjacent slits in the series. Generally it is preferred that the gaps are regularly sized.

Preferably the body comprises two or more parallel linear series of slits, each linear series being spaced from the adjacent linear series. Preferably the spacing between the adjacent linear series is regular.

It will be clear to the person skilled in the art that the size of the gap between the slits, and the spacing between adjacent series, must be sufficient such that the material retains structural integrity sufficient for it to be handled, used in therapy and removed thereafter without breaking up. If the gaps and spacing were too small, the body would be too weak to achieve this. On the other hand, there is a desire to maximise the size and density of the slits to maximise drapeability. It is preferred that the minimum size of the gaps and/or spacing should certainly be no less than the average pore diameter. It is more preferred that gaps and/or spacing are at least 5 times the average pore diameter; given that the average pore diameter for NPWT foam is in the range of 300-800 μm, this gives a gap or spacing of 1500 to 4000 μm, i.e. 1.5 to 4 mm. A gap of around 3 mm has been found to be particularly effective in a typical NPWT, though there is of course scope to vary this.

It is preferable that the spacing between adjacent linear series of slits is kept reasonably small to provide the desired amount of flexibility and hence drapeability. Accordingly, it is preferred that the spacing is not more than 50 times the average pore diameter (typically from 15 mm to 40 mm depending on pore density), preferably not more than 30 times than average pore diameter (typically from 9 mm to 24 mm depending on pore density). A spacing of around 3 mm has been found to be particularly effective in a typical NPWT, though there is of course scope to vary this.

It is preferred that, where two or more parallel linear series of slits are provided, adjacent series are linearly offset relative to each other, i.e. it is preferred that the slits and gaps in adjacent series do not line up, but are staggered. To put it another way, adjacent series may be out of phase with each other. In one embodiment adjacent series are offset such that the centre point of a slit in one series is aligned approximately with the gap in an adjacent series—similar to the way layers of bricks are offset in a wall. There is of course scope to vary the amount of offset.

This offset of adjacent series of slits allows for particularly good drapeability. When the body is curved the slits open up to form a lattice type structure which is particularly suited to provide good flexibility, and hence drapeability.

The slits may suitably pass completely through the thickness of the body. Alternatively the slits may pass only partially though the thickness of the body, provided they pass through far enough to provide the desired flexibility to the body. In general it is preferred that the slits pass at least half way through the thickness of the body, preferably at least three quarters of the way through the body, and especially substantially all the way through the body.

The present application is particularly suited to a wound dressing material comprising a body of porous material which is relatively thin, although it could be used to impart flexibility to a body which is thick. In particular, the present invention is particularly suited to a sheets of porous material which have a thickness of from 5 mm to 75 mm, preferably from 10 mm to 50 mm, especially from 15 to 40 mm, most preferably from 20 to 35 mm. In a very thin sheet (less than 5 mm) drapeability of the sheet is not such an issue, and where the thickness is greater than about 75 mm, providing a plurality of cuts becomes less effective as a means of introducing flexibility. Thus the ranges set out above represent sheets of thicknesses which are particularly well suited to the present invention. The other dimensions of the sheet are not particularly significant, although it may be observed that NPWT foam is typically sold in generally cuboid sheets with the dimensions of the edges of largest face being between 100 and 200 mm, e.g. a sheet measuring 100×200×30 mm is fairly typical.

It is generally preferred that the cuts are provided passing through the shortest dimension of the body. In particular it is preferred that the cuts (e.g. slits) are provided passing between the two largest faces of a cuboid body (e.g. sheet), and especially that the cuts are perpendicular to the largest faces.

Where two or more parallel linear series of slits are provided, as set out above, this provides for good flexibility in a single direction of curve. When a body is curved around a surface, the inside of the body is subject to compression and the outside of the body is subjected to tension (inside and outside being defined relative to the curve). In wound dressings according to the present invention the cuts allow the body to stretch when under tension, the cuts allowing deformation of the shape of the body (e.g. into a lattice), and this allows the body to easily adapt to the desired curve. Where the cuts comprise slits in a single orientation, the body will be well adapted to curving in a direction which causes tension perpendicular to the slits, but will be less well adapted to curving in another direction, i.e. where the tension produced is parallel to the slits. Therefore, the body is well suited to drape around a body with a single curvature (e.g. generally cylindrical), but not so well suited to draping around a more complex curved object such as a generally spherical shape.

In a further embodiment of the present invention, the body comprises a second set of slits passing at least partially through the body in a different orientation (preferably perpendicular) to the slits in the at least one linear series of slits described above (the "first set of slits"). It is preferred that the second set of slits also pass between, and are perpendicular to, the largest faces of the body. Additional slits provided in this manner allow the body to curve more easily in a second direction thus making it more suited to adapting to a complex curved surface, i.e. curved in two planes.

In a preferred embodiment of the invention at least some of the slits in both orientations intersect. Suitably the intersection of the slits effectively provides a two-dimensional (2-D) slit. Preferably the 2-D slit has an H shape, with a two parallel slits in one orientation being intersected at their mid-points by a third slit in a perpendicular orientation. Such an H-shaped 2-D slit is well suited to the provision of a relatively dense array of 2-D slits in the body. For example, rows of H-shaped slits, each adjacent slit within the row alternating in orientation by 90 degrees, can be packed closely together, while obeying the minimum spacing requirements set out above.

In a preferred embodiment of the invention, the body comprises a first set of parallel linear series of H-shaped slits in a first orientation and a second set of parallel linear series of H-shaped slits in a second orientation. Preferably the second orientation is perpendicular to the first orientation. Preferably adjacent series within a set are offset relative to one another. Such an arrangement allows very close packing of the H-shaped slits, whilst maintaining a suitable spacing between neighbouring slits to retain the overall structural integrity of the body. To allow close packing of the slits it is preferred that the length of the two parallel slits (the "sides") of the H-shaped slit are shorter than the perpendicular slit (the "cross-piece") of the H-shaped slit. For example, the "cross-piece" may be from 10 mm to 70 mm in length, preferably from 20 mm to 50 mm, especially from 25 mm to 40 mm, most preferably 30 mm and the "sides" are preferably around 6 mm shorter than the "cross-piece", especially around half the length of the "cross-piece". Where the "sides" of the H are shorter than the "cross-piece", it allows the "sides" of H-shaped slits in one orientation to nest within the area bounded by "sides" and "cross-piece" of the H-shaped slit in the other orientation. This allows for very close packing of the H-shaped slits.

It should be noted that while a body having an array of H-shaped 2-D slits is a preferred embodiment of the present invention, it is possible to achieve a suitable 2-D array using other shapes, such as cruciform slits, or the like.

It should be noted that the cuts, e.g. slits, of the present invention can be provided by cutting a preformed body of foam, or the cuts could be provided during the process in which the body is manufactured (e.g. moulding). It is preferred that the cuts are provided by die cutting a preformed body.

In a further aspect, the present invention provides a method of manufacturing a wound dressing, the method comprising the steps of;

providing a body of a porous material; and providing a plurality of cuts which provide regions of flexibility within the body.

It is preferred that the cuts are provided by die cutting using an array of suitably sized and shaped blades to provide the desired cuts.

Details of preferred cuts, e.g. slits, are set out above, and it will be obvious to the person skilled in the art how to provide a suitable blade to achieve the desired cut.

The cuts may be provided all the way through the body, or they may only pass partially through the body.

The cuts may be formed in a batch, or they may be formed in a flow process.

In a further aspect the present invention provides a method of dressing a wound comprising administering a wound dressing as set out above to the wound.

Preferably the method provides the step of applying a negative pressure to the wound through the wound dressing material, i.e. the method is NPWT. In general this can be achieved by providing a substantially fluid impermeable sheet over the wound and wound dressing, thus defining a sealed volume, and applying a negative pressure inside said sealed volume. The seal need not be completely hermetic, but should be sufficient to allow a suitable negative pressure to be sustained. The source of negative pressure, e.g. a pipe form a vacuum pump, can be provided at a position such that it draws fluids from the wound bed through the wound dressing material.

Suitably the negative pressure is in the range of from 80 to 125 mm Hg below ambient atmospheric pressure.

In a further aspect the present invention provides the use of a wound dressing material as set out above in wound treatment, especially NPWT.

BRIEF DESCRIPTION OF THE DRAWINGS

Other features and advantages of the present invention will be apparent from the following detailed description of the invention, taken in conjunction with the accompanying drawings of which.

Figure 6:
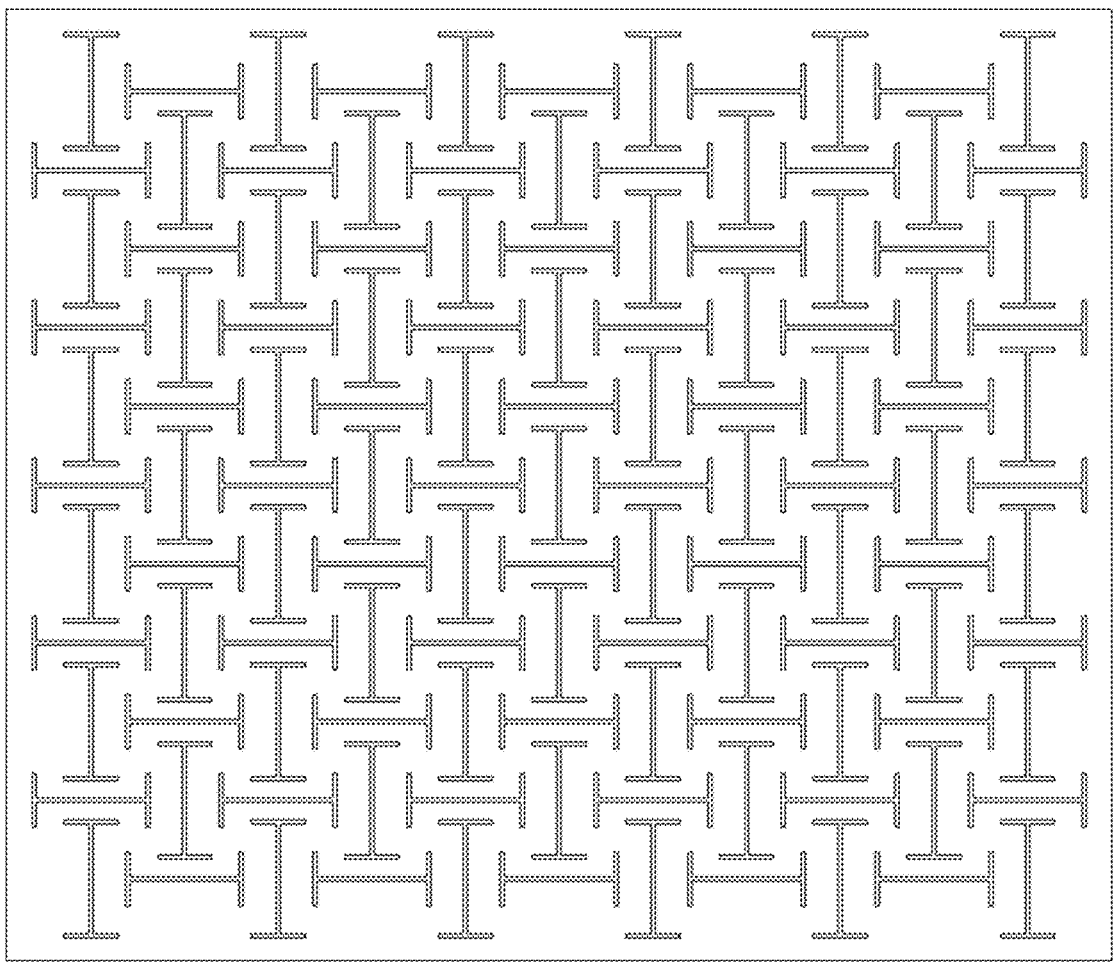
FIG. 6 is a schematic in plain view of yet a further a cutter, having an alternative cutting profile to the cutter of FIGS. 2 and 4, for use in the manufacture of a third embodiment of the lattice according to the invention.
Figure 7:
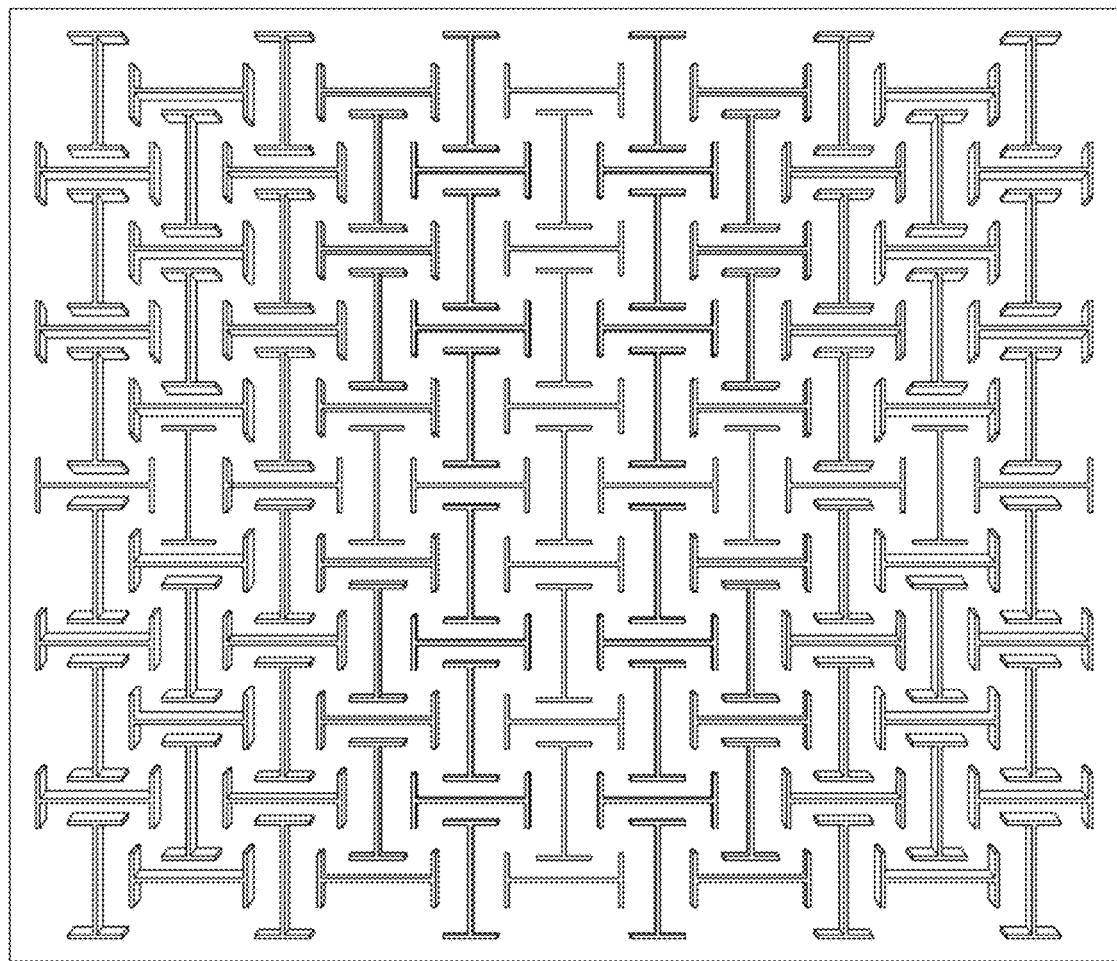

FIG. 7 is a plan view of the cutter manufactured according to the schematic of FIG. 6.

Figure 8:
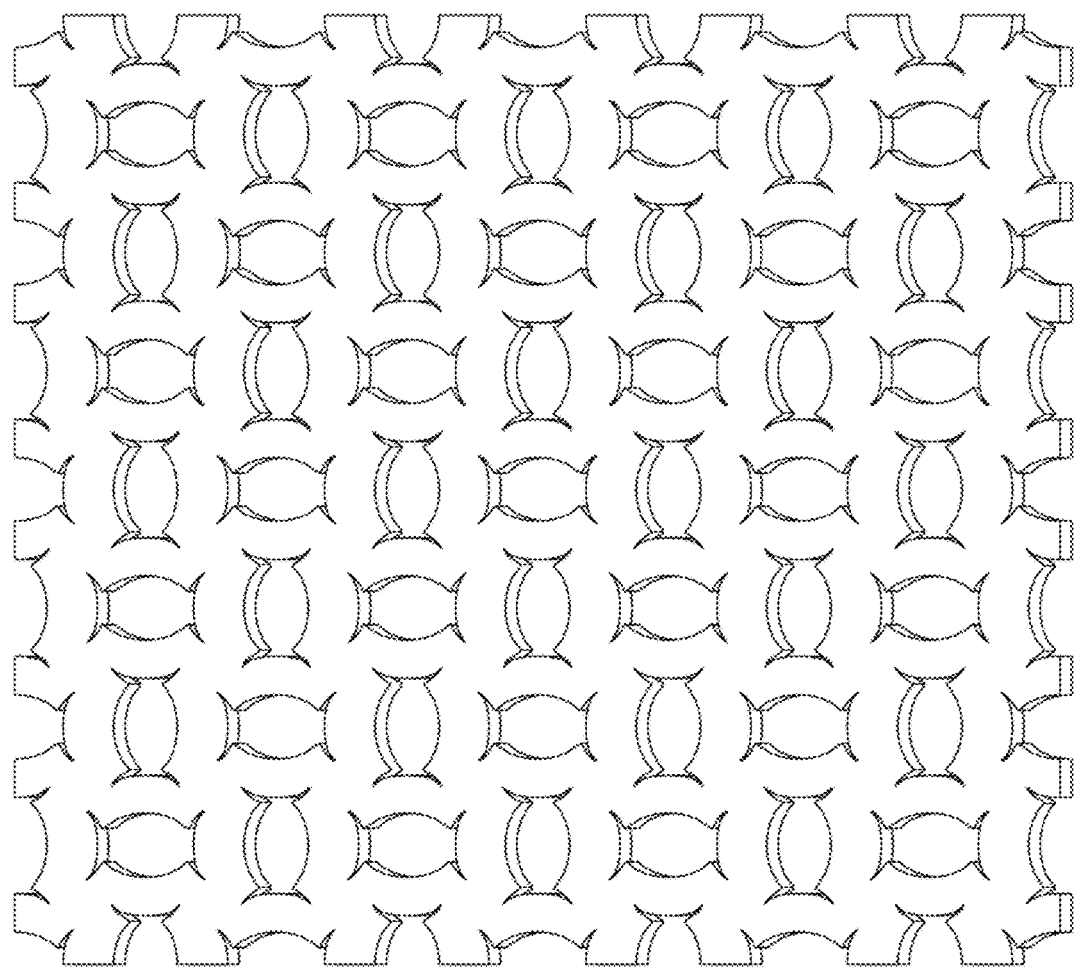

FIG. 8 is a plan view of the lattice formed using the cutter of FIG. 7, the lattice shown here in the open lattice or second conformation on application of a bi-directional extensive force applied perpendicular and parallel to the longitudinal axis of the slits.

Figure 9:
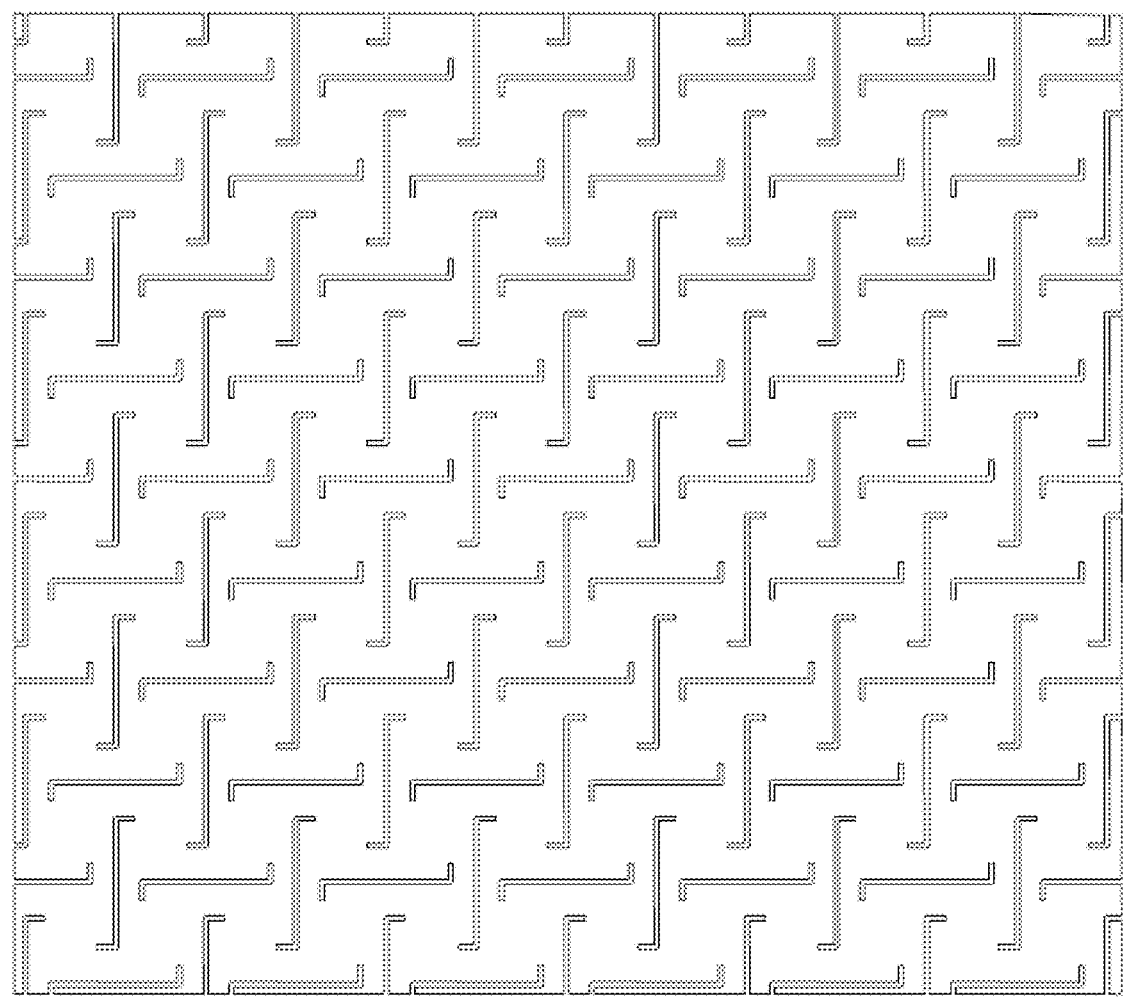

FIG. 9 is a plane view of the lattice in the first conformation where the slits are substantially closed. The lattice is opaque and the slits allow for no or substantially no visual inspection across the lattice.

Figure 10:
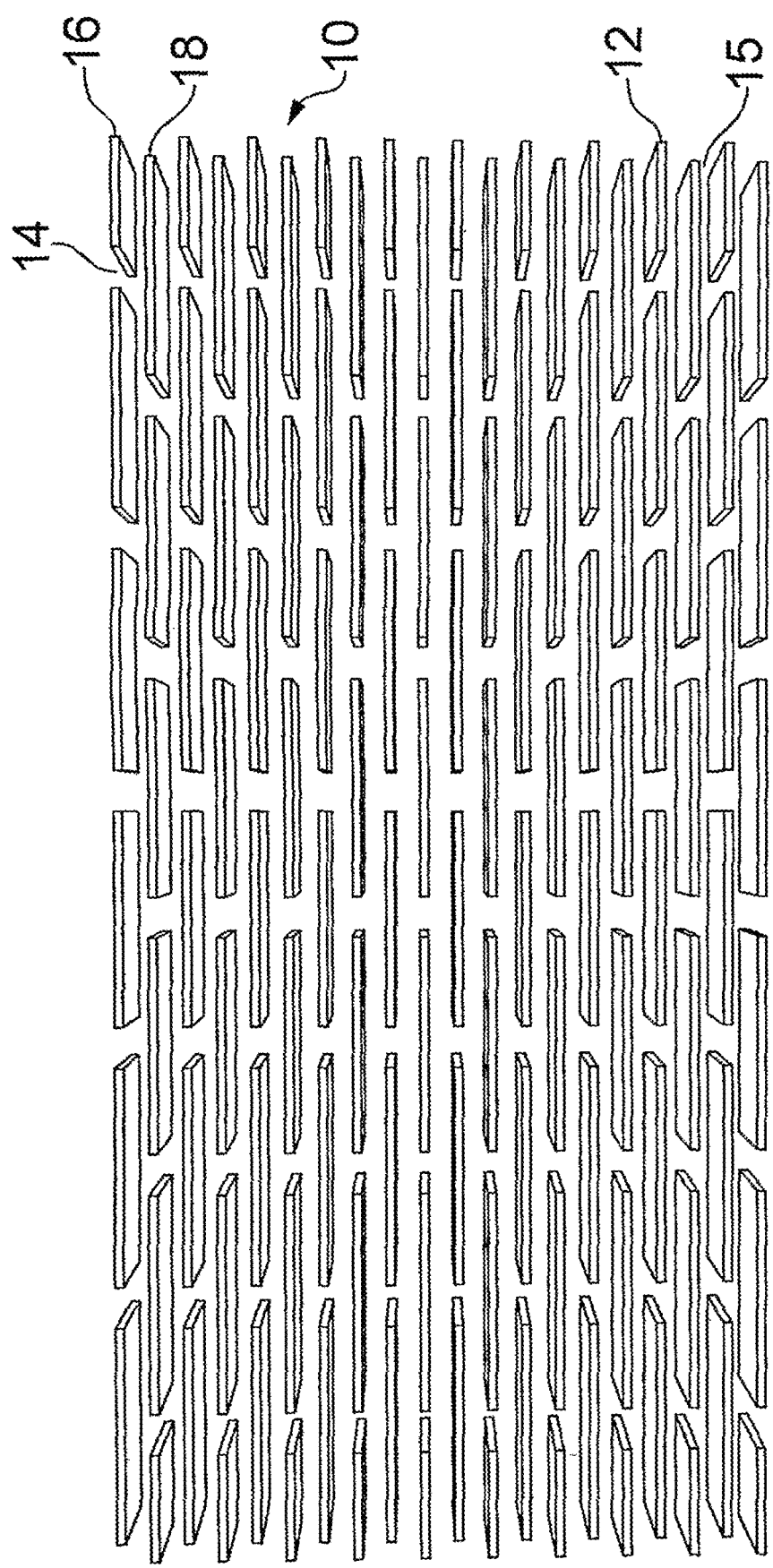
Figure 11:
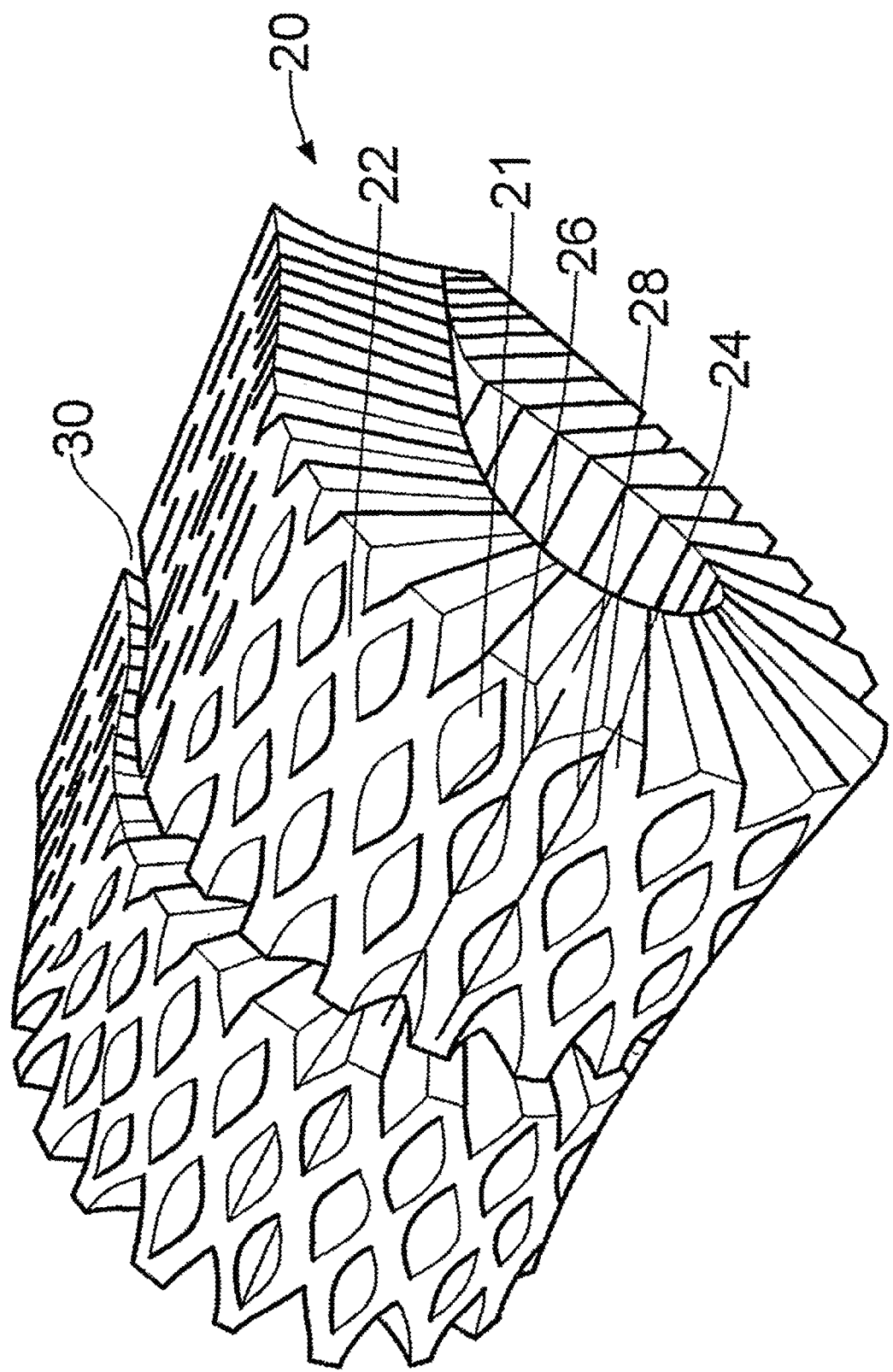
Figure 12:
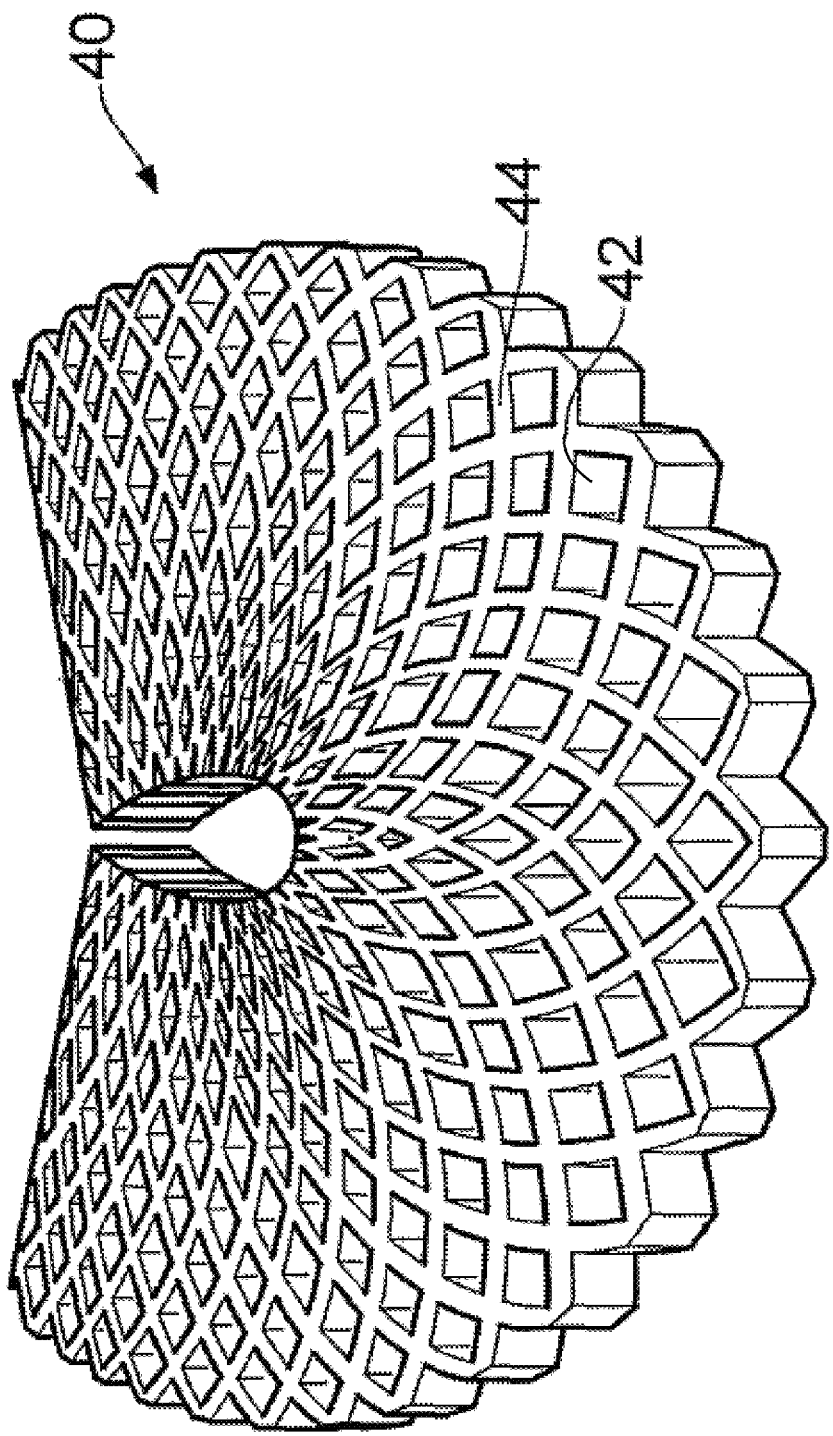
Figure 13:
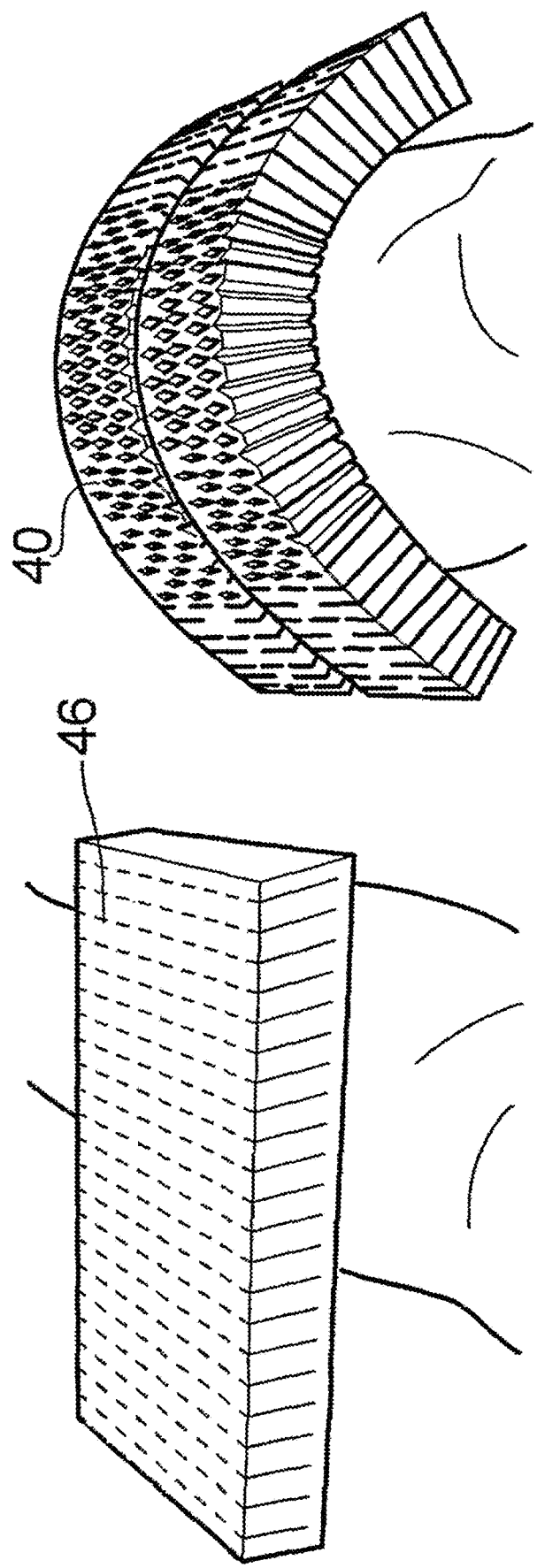
Figure 14:
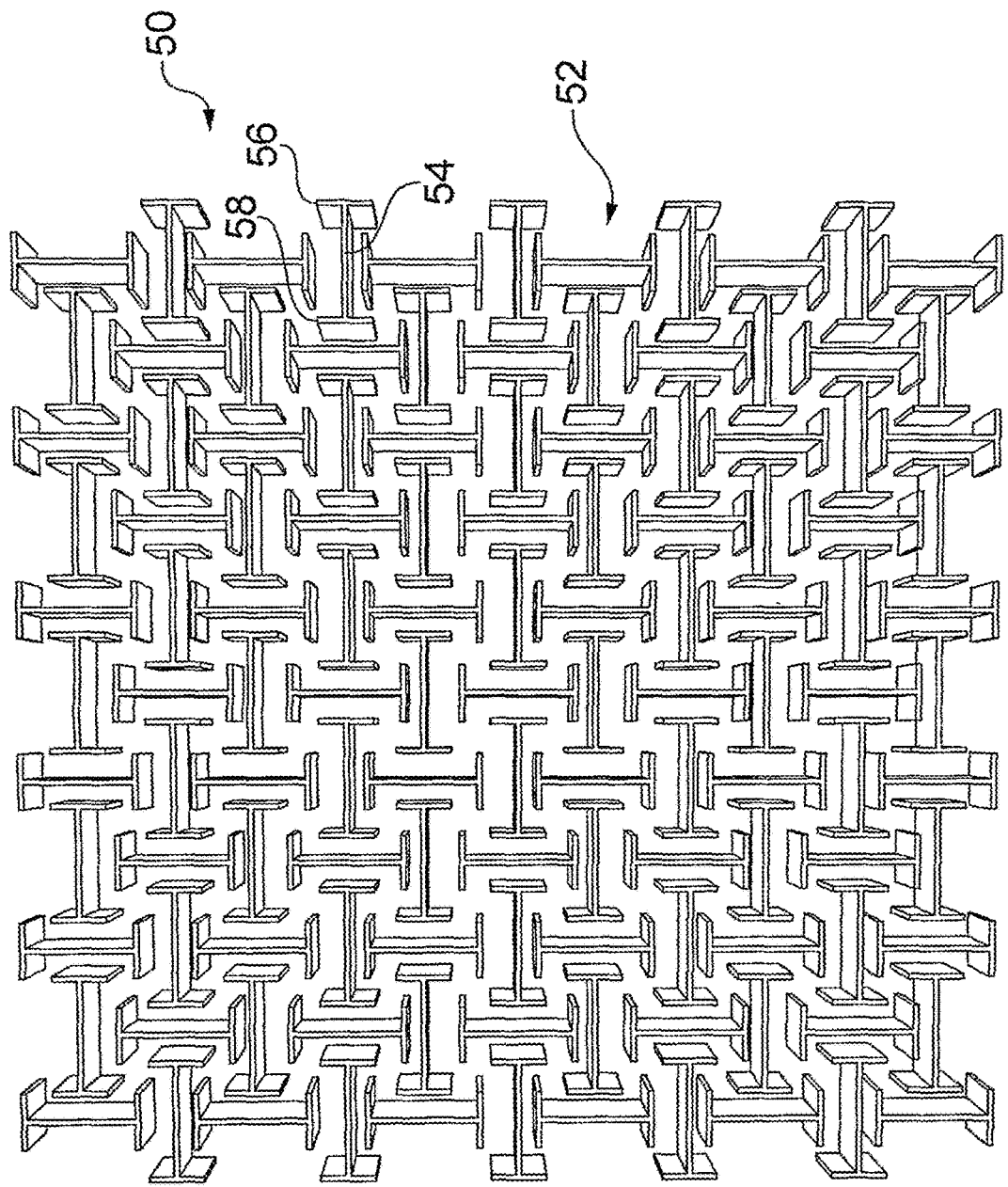
Figure 15:
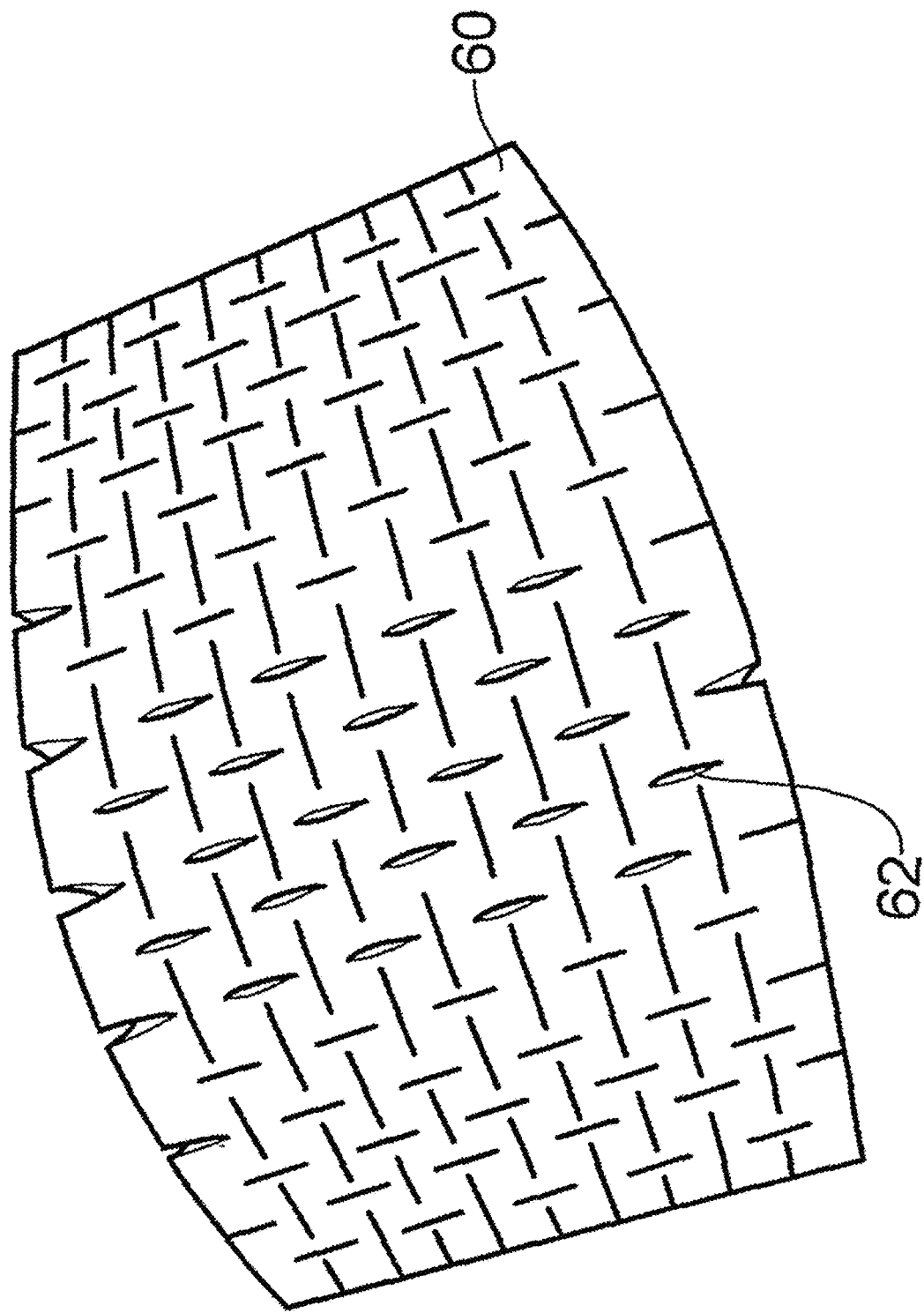
Figure 16:
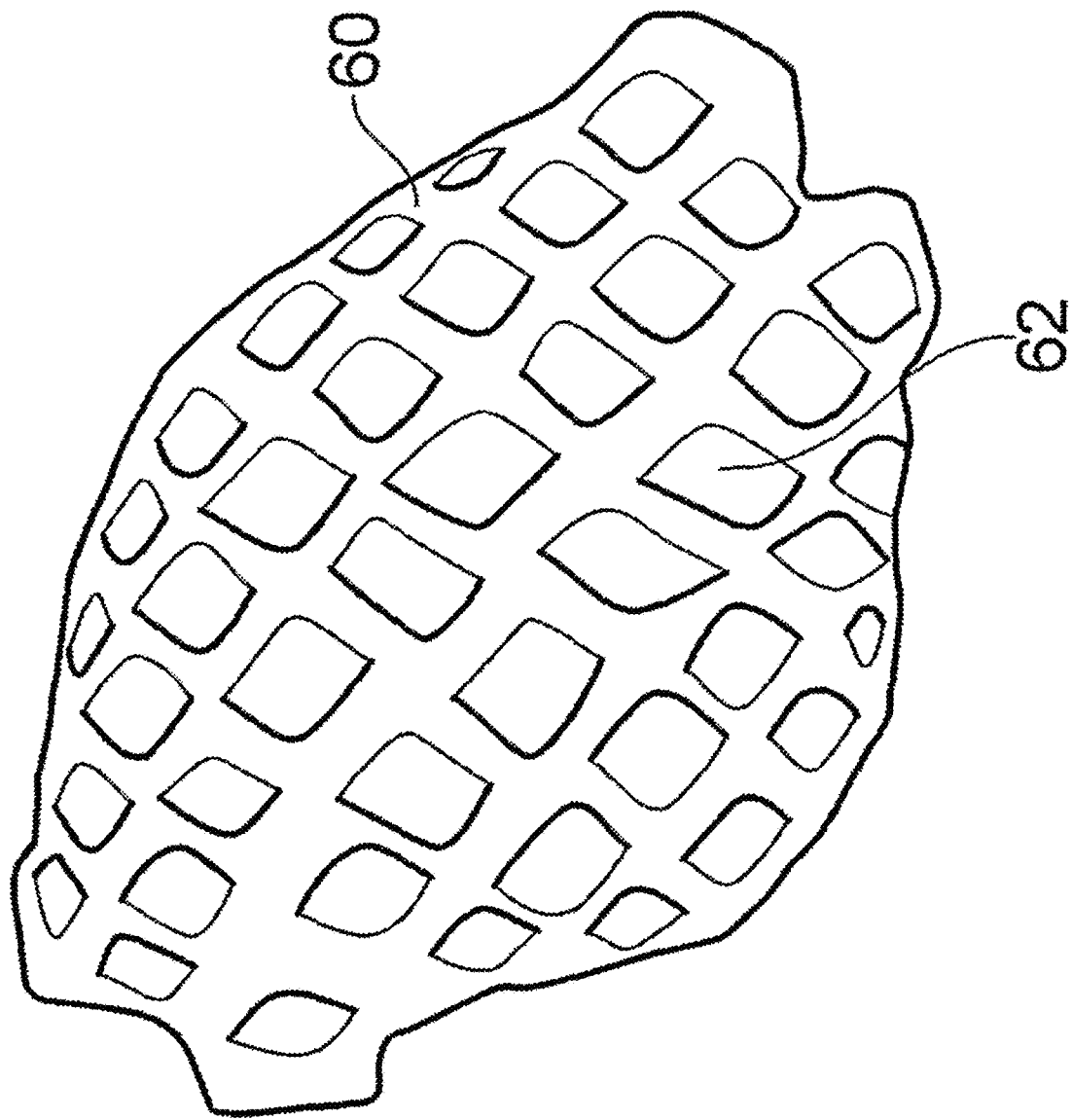

FIG. 10 shows an array of blades adapted to form slits in a body of a wound dressing material according to the present invention;

FIG. 11 shows a body according to the present invention curved in a first direction;

FIG. 12 shows a body according to the present invention curved in a second direction;

FIG. 13 shows a comparison of a body of foam according to the present invention with an un-cut body of foam;

FIG. 14 shows a second array of blades adapted to form cuts in a body of a wound dressing material according to the present invention;

FIG. 15 shows a body according to the present invention cut with the array of blades of FIG. 14; and FIG. 16 shows the body of FIG. 15 curved in two dimensions.

Figure 17:
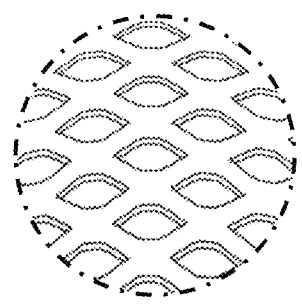

FIG. 17 shows a portion of an embodiment of a lattice.

DETAILED DESCRIPTION OF THE PREFERRED EMBODIMENTS

Like reference numbers refer to corresponding parts throughout the drawings, description and examples.

EXAMPLE 1

To create the wound dressing of example 1, a perforated sheet of polyurethane film was applied to the wound contact surface of a sheet of 4 mm depth polyurethane foam (Allevyn, Smith & Nephew Medical Limited).

The wound contact surface is that surface which is placed adjacent to or in direct contact with the wound. The non-wound contact surface is that surface which is remote from or opposite the wound contact surface.

Figure 1:
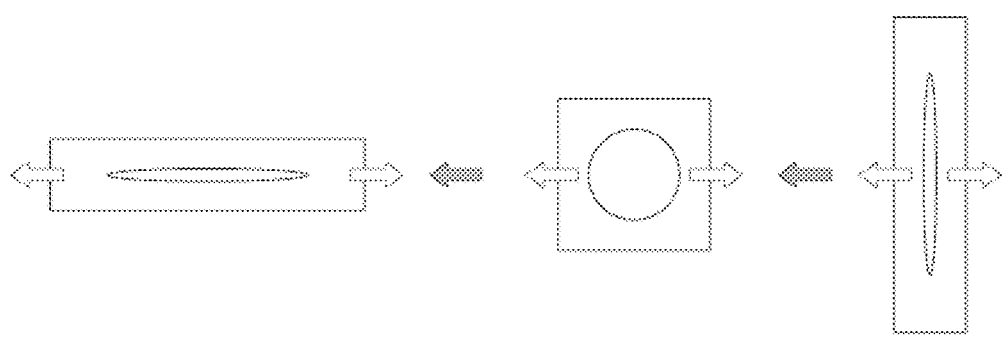
FIG. 1 demonstrates the extension of a slit, in three stages, under an extensive force, indicated by the arrows F, and in a direction perpendicular to the longitudinal axis of the slit. The intermediate or second stage shows that the slit has been expanded to form a circle.
Figure 2:
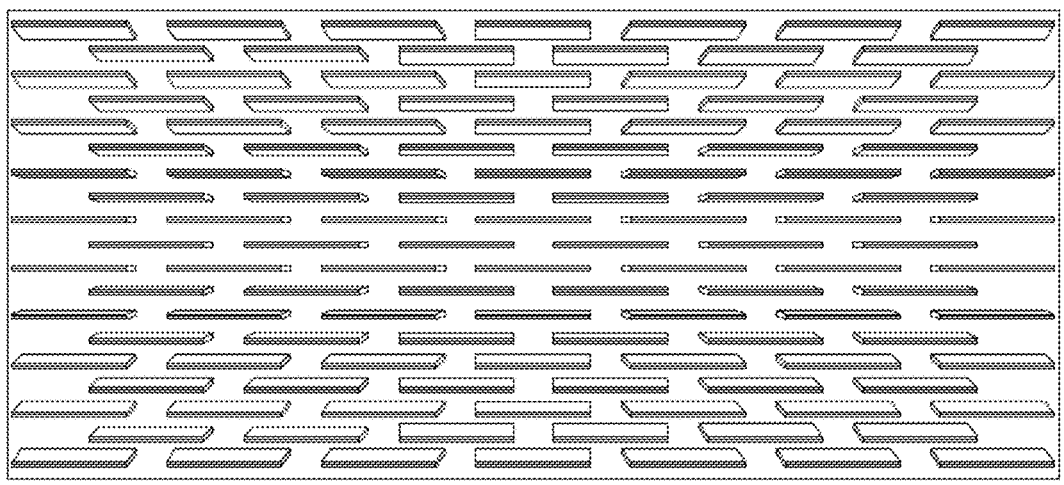
FIG. 2 is a plan view of a cutter for use in the manufacture of a first embodiment of lattice according to the invention.

A cutter of specification shown in FIG. 2 (Cutter blade with 15 mm length blades, linear spacing 5 mm, vertical spacing 5 mm) was used to cut slits in the sheet of polyurethane foam to form a lattice. The cutting action also formed slits in the polyurethane film.

Figure 3:
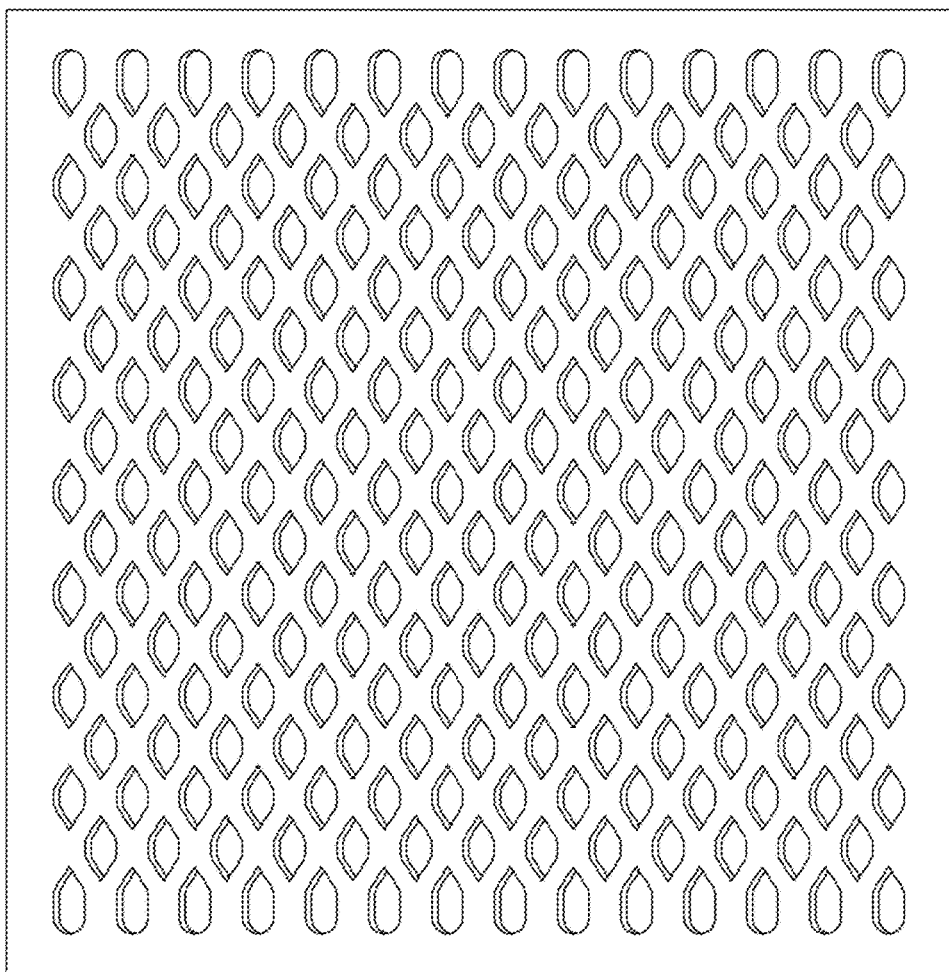
FIG. 3 is a plan view of the lattice formed using the cutter of FIG. 2, the lattice shown here in the open lattice or second conformation on application of a uni-directional extensive force applied perpendicular to the longitudinal axis of the slits.

Following cutting, an extensive force was applied to the lattice in a direction perpendicular to the longitudinal axis of the cuts or slits to produce an open lattice as shown in FIG. 3. A moisture permeable top-film was heat laminated to the non-wound contact layer or surface of the open lattice. To the top-film, a polymeric film release sheet of sufficient mechanical stiffness to resist the contractile force of the open lattice was applied. After applying the release sheet the extensive force applied to the lattice was removed and the extended or open lattice was retained in the open lattice conformation by the release sheet.

EXAMPLE 2

To create the wound dressing of example 2, a perforated sheet of adhesive polyurethane film was applied to the wound contact surface of a sheet of 4 mm depth polyurethane foam (Allevyn, Smith & Nephew Medical Limited). The adhesive surface of the film was covered by a siliconised release paper. A cutter of specification shown in FIG. 2 (Cutter blade with 15 mm length blades, linear spacing 5 mm, vertical spacing 5 mm) was used to cut slits in the sheet of polyurethane foam to form a lattice. The cutting action also formed slits in the polyurethane film and siliconised release paper.

The wound contact surface is that surface which is placed adjacent to or in direct contact with the wound. The non-wound contact surface is that surface which is remote from or opposite the wound contact surface.

Following cutting, the siliconised release paper was removed and an extensive force was applied to the lattice in a direction perpendicular to the longitudinal axis of the cuts or slits to produce the open lattice pattern as shown in FIG. 3. A new sheet of siliconised release paper was then attached to the wound contact surface of the perforated adhesive film. A moisture permeable top-film was heat laminated to the non-wound contact layer or surface of the open lattice. To the top-film, a polymeric film release sheet of sufficient mechanical stiffness to resist the contractile force of the open lattice was applied. After applying the release sheet the extensive force applied to the lattice was removed and the extended or open lattice was retained in the open lattice conformation by the release sheet.

EXAMPLE 3

To demonstrate the effectiveness of the wound dressing of example 2, the siliconised release paper was removed from the perforated adhesive film and placed, adhesive side down, upon intact skin. The polymeric film release sheet was then removed. A uni-directional contractile force was generated on the skin, upon removal of the polymeric film release sheet, and in a direction perpendicular to the axis of the cuts.

EXAMPLE 4

To create the wound dressing of example 4, a perforated sheet of polyurethane film was applied to the wound contact surface of a sheet of 4 mm depth polyurethane foam (Allevyn, Smith & Nephew Medical Limited). A cutter of specification shown in FIG. 4 (Cutter blade with 15 mm length blades, linear spacing 5 mm, vertical spacing 2.5 mm) was used to cut slits in the sheet of polyurethane foam to form a lattice. The cutting action also formed slits in the polyurethane film and siliconised release paper.

The wound contact surface is that surface which is placed adjacent to or in direct contact with the wound. The non-wound contact surface is that surface which is remote from or opposite the wound contact surface.

Figure 4:
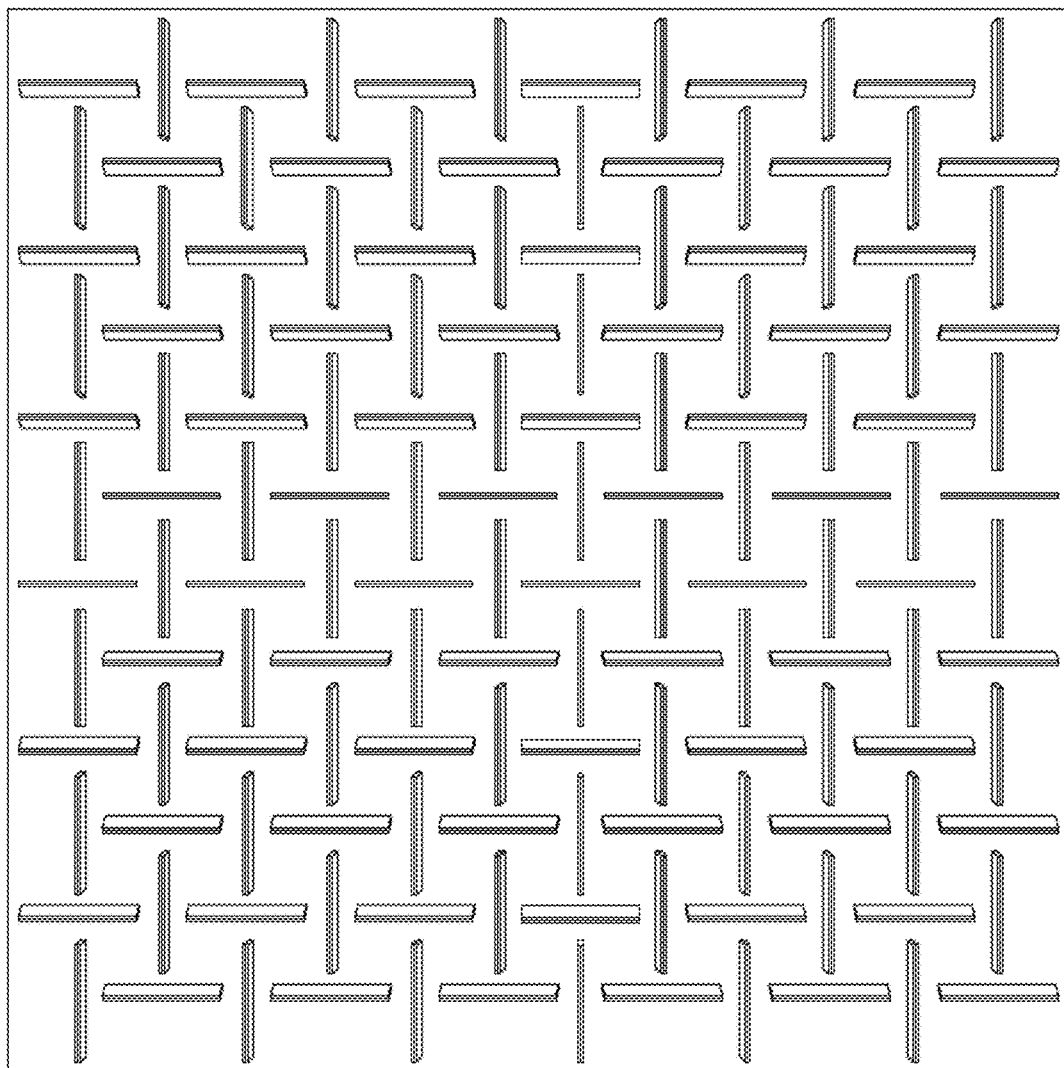
FIG. 4 is a plan view of a further cutter having a different cutting profile to the cutter of FIG. 2 for use in the manufacture of a second embodiment of lattice according to the invention.

Following cutting, the lattice was extended along two axes, x and y, as shown in FIG. 4. The extensive force was applied perpendicular and parallel to the longitudinal axis of the slits to produce an open lattice structure. A moisture permeable top-film was heat laminated to the non-wound contact surface of the open lattice. To the top-film, a polymeric film release sheet of sufficient mechanical stiffness to resist the contractile force of the open lattice was applied. After applying the release sheet the extensive force applied to the lattice was removed and the extended or open lattice was retained in the open lattice conformation by the release sheet.

EXAMPLE 5

To create the wound dressing of example 5, a perforated sheet of adhesive polyurethane film was applied to the wound contact surface of a sheet of 4 mm depth polyurethane foam (Allevyn, Smith & Nephew Medical Limited). The adhesive surface of the film was covered by a siliconised release paper. A cutter of specification shown in FIG. 4 (Cutter blade with 15 mm length blades, linear spacing 5 mm, vertical spacing 2.5 mm) was used to cut slits in the sheet of polyurethane foam to form a lattice. The cutting action also formed slits in the polyurethane film and siliconised release paper.

The wound contact surface is that surface which is placed adjacent to or in direct contact with the wound. The non-wound contact surface is that surface which is remote from or opposite the wound contact surface.

Following cutting, the siliconised release paper was removed and the lattice was extended along two axes, x and y, as shown in FIG. 4. The extensive force was applied perpendicular and parallel to the longitudinal axis of the slits to produce an open lattice structure. A new sheet of siliconised release paper was then attached to the wound contact surface of the perforated adhesive film. A moisture permeable top-film was heat laminated to the non-wound contact layer or surface of the open lattice. To the top-film, a polymeric film release sheet of sufficient mechanical stiffness to resist the contractile force of the open lattice was applied. After applying the release sheet the extensive force applied to the lattice was removed and the extended or open lattice was retained in the open lattice conformation by the release sheet.

Figure 5:
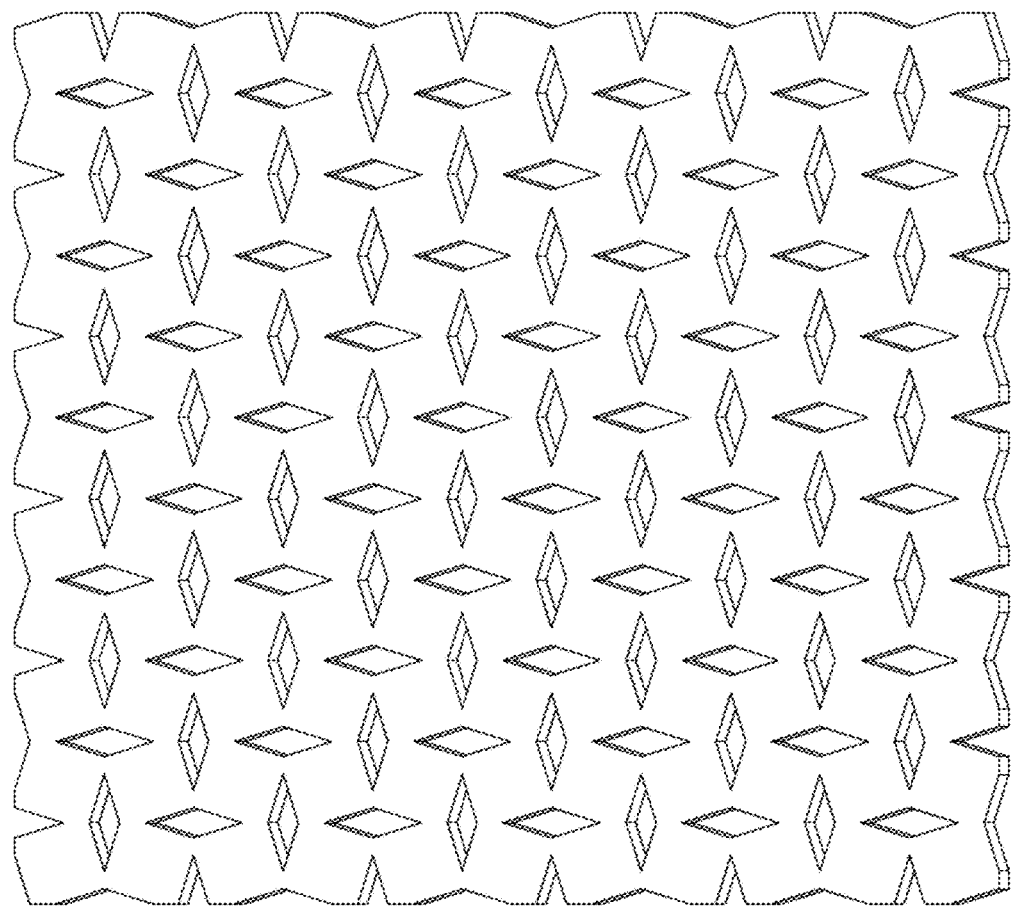
FIG. 5 is a plan view of the lattice formed using the cutter of FIG. 4, the lattice shown here in the open lattice or second conformation on application of a bi-directional extensive force applied perpendicular and parallel to the longitudinal axis of the slits.

The lattice of the wound dressing of example 5, having the polymeric film release sheet removed, it shown in FIG. 5.

EXAMPLE 6

To demonstrate the effectiveness of the wound dressing of example 5, the siliconised release paper was removed from the perforated adhesive film and placed, adhesive side down, upon intact skin. The polymeric film release sheet was then removed. Upon removal of the polymeric film release sheet, a contractile force was generated on the skin acting towards the centre of the dressing.

EXAMPLE 7

A similar process to that described for the wound dressing of example 5 is employed to create the wound dressing of example 7. However, in this case, a cutter of specification shown in FIGS. 6 and 7 was used to cut the slits. As can be seen from FIG. 6, the blades have three cutting edges. A long cutting edge of 15 mm in length bridging two shorter cutting edges of 7 mm in length. The two shorter cutting edges being parallel to each other and perpendicular to the longer cutting edge. Each blade has a spacing with an adjacent blade which describes a square area having a side length of 3.75 mm. This spacing is demonstrated by the shaded square portion in FIG. 6.

The lattice of the wound dressing of example 7, having the polymeric film release sheet removed, it shown in FIG. 8.

An array of blades (10) mounted on a board is shown in FIG. 10. Each blade (12) is a straight thin blade 30 mm long, and having a depth of approximately 30 mm. The blades are arranged in 20 parallel linear series of blades (16,18), each series comprising a row of blades (12) arranged longitudinally, with a gap (14) of 3 mm between each blade (12) in the series. Each series is spaced from the adjacent series by a 3 mm spacing (15). Furthermore, adjacent series (16,18) are staggered relative to one another such that the gap between the blades on one series (16) aligns with the midpoint in the adjacent series (18). Accordingly, the blades within the array (10) are arranged like the bricks in a wall. Given this offset arrangement, it is convenient that at the end of a series where a full 30 mm blade would extend beyond the dimension to be cut, blades of 15 mm length are provided; this allows for a neater array—once more, this is akin to half bricks at the end of a row in a wall. Full length blades could be used at the ends, provided they would not be problematic in the cutting process.

A body of NPWT foam (20) measuring 200×125×30 mm is cut using the array (10). It is cut by driving the array of blades (10) through the body (20) in a die cutting operation. This can be achieved using a press, typically a hydraulic press (not shown), also known as a clicker press. The blades are driven perpendicularly into and through the largest face of the body (20), and perpendicular thereto, to form a plurality of slits therein. The slits (21) formed are arranged in a plurality of parallel linear series (26,28) of slits, each comprising slits (21) 30 mm long separated by gaps (22), where material is left un-cut, which are 3 mm long. Each series is separated by a spacing (24) 3 mm in width. When the body (20) is curved, as shown in FIG. 11, the slits (21) open up to form a lattice structure. Tension in the outer region of the body (20) as a result of the curving process is relieved through deformation of the body (20) which is facilitated by the slits (21) provided therein. The arrangement of parallel offset linear series of linear slits is particularly suited to this as it form a regular lattice structure, as shown in FIG. 11.

In the embodiment shown in FIG. 11, an additional partial cut (30) has been made running the length of the middle of the largest face of the body (20), perpendicular to the slits. This allows the body (20) to be easily split in two if this is desirable.

FIG. 12 shows another body (40) cut using the array of blades of FIG. 10, this time without the additional cut (30). The body has been curved in a different manner to that in FIG. 11. In this case the body has been bent back on itself along its longest side, i.e. the 200×300 mm face has been curved back on itself. The body (40) has opened via the slits (42) into an open lattice structure. This type of curving of the body (40) is not generally useful for a wound dressing application, but does serve to demonstrate the flexibility and strength of the body (40).

FIG. 13 further demonstrates the ability of a body according to the present invention (40) to drape over a surface, in this case a leg, when compared to an uncut body (46).

FIG. 14 shows an array (50) of blades adapted to form cuts in a body of foam in two orientations, the orientations being perpendicular to each other. As with the array (10) in FIG. 10, the blades have a depth of 30 mm. However, in the array (50) comprises H-shaped blades (52) comprising a first blade element 30 mm long (54) (also termed "cross-piece"), with second (56) and third (58) blade elements (also termed "sides") 15 mm long located at the end of the first blade element (54), each end of the first blade element intersecting with the midpoint of the second and third blade elements, thus defining a "wide H-shaped" blade. The array is made up of first set of eleven parallel linear series of H-shaped blades in a first orientation (called X for convenience) and a second set of eleven parallel linear series of H-shaped blades in a second, perpendicular orientation (called Y for convenience). Adjacent series within each set are offset in exactly the same manner as for linear blades. As can be seen from FIG. 14, the blades are spaced and arranged such that a close packing of the blades as achieved, but each blade is always approximately 5 mm or so from the nearest neighbouring blade. It can be seen that the "side" of a blade in the X-orientation nests within the region defined by the "crosspiece" and "sides" of a blade in the Y-orientation. Such an array is suited to forming slits in a body to allow draping in two planes.

FIG. 15 shows a body (60) formed by cutting with the array of FIG. 14. The slits (62) are formed by pressing the array of blades (50) through the body (60) in the same manner as described above. H-shaped slits (62) are formed in the body (60) corresponding to the array of blades (50). As shown in FIG. 16, the body (60) is well adapted to curving in complex shapes.

It should be noted that the present description has focused on bodies formed by a batch die cutting process. There are of course numerous ways of forming cuts in a body of porous material (e.g. laser cutting, high pressure liquid cutting), or the cuts could formed when the body itself is formed (e.g. during a moulding process). Furthermore, these methods could be applied in a flow process rather than a batch; this might be more efficient for large production runs. All such variations are within the scope of the present invention.

Furthermore, it should be noted that, while the exemplified embodiments form particularly preferred embodiments with excellent drapeability, it is quite possible that other arrangements of cuts will provide satisfactory results.

What is claimed is:

1. A wound treatment apparatus, comprising:
    a perforated foam layer, comprising:
        a foam body; and
        a first series of apertures extending all the way through the foam body, wherein:
            the first series of apertures comprises a plurality of curved apertures arranged in an end to end pattern; and
            the first series of apertures has a plurality of gaps between each of the plurality of curved apertures where the material is left uncut;
        a second series of apertures extending all the way through the foam body, wherein:
            the second series of apertures comprises a plurality of curved apertures arranged in an end to end pattern;
            the second series of apertures has a plurality of gaps between each of the plurality of curved apertures where the material is left uncut;
            the plurality of curved apertures of the second series of apertures are offset from the plurality of curved apertures of the first series of apertures so that each of the curved apertures of the second series of apertures is staggered relative to each of the curved apertures of the first series of apertures and so that each of the gaps of the second series of apertures is staggered relative to each of the gaps of the first series of apertures; and
            the plurality of curved apertures of the first series of apertures are arranged in an end to end pattern along a curved path when the foam layer is in an initial conformation.

2. The wound treatment apparatus of claim 1, wherein the plurality of curved apertures of the second series of apertures are offset from the plurality of curved apertures of the first series of apertures so that a center point of an aperture of the second series of apertures is aligned approximately with the gap of the first series of apertures.

3. The wound treatment apparatus of claim 1, further comprising a third series of apertures extending all the way through the foam body, wherein:
    the third series of apertures comprises a plurality of curved apertures arranged in an end to end pattern;
    the third series of apertures has a plurality of gaps between each of the plurality of curved apertures where the material is left uncut;
    each of the plurality of curved apertures of the third series of apertures forms an aperture in the foam body; and
    the plurality of curved apertures of the third series of apertures are offset from the plurality of curved apertures of the second series of apertures so that each of the curved apertures of the third series of apertures is staggered relative to each of the curved apertures of the second series of apertures and so that each of the gaps of the third series of apertures is staggered relative to each of the gaps of the second series of apertures.

4. The wound treatment apparatus of claim 3, further comprising a fourth series of apertures extending all the way through the foam body, wherein:
    the fourth series of apertures comprises a plurality of curved apertures arranged in an end to end pattern;
    the fourth series of apertures has a plurality of gaps between each of the plurality of curved apertures where the material is left uncut;
    each of the plurality of curved apertures of the fourth series of apertures forms an aperture in the foam body; and
    the plurality of curved apertures of the fourth series of apertures are offset from the plurality of curved apertures of the third series of apertures so that each of the curved apertures of the fourth series of apertures is staggered relative to each of the curved apertures of the third series of apertures and so that each of the gaps of the fourth series of apertures is staggered relative to each of the gaps of the third series of apertures.

5. The wound treatment apparatus of claim 1, wherein nearly an entire first surface of the foam body is covered by curved apertures.

6. The wound treatment apparatus of claim 1, wherein, when the perforated foam layer is stretched by the application of an extensive force to the perforated foam layer, the first series of apertures and the second series of apertures both expand so that the apertures of the first series of foam apertures and the apertures of the second series of foam apertures expand.

7. The wound treatment apparatus of claim 1, wherein the first and second series of apertures provide macroscopic flexibility to the perforated foam layer to allow the perforated foam layer to drape more easily to conform to the shape of a wound.

8. The wound treatment apparatus of claim 1, wherein the foam body has a thickness of from 15 mm to 40 mm.

9. The wound treatment apparatus of claim 1, wherein the plurality of curved apertures of the first and second series of apertures extend through a thickness of the foam body.

10. The wound treatment apparatus of claim 1, wherein the plurality of apertures of the first and second series of apertures are formed by cutting slits in the foam body.

11. The wound treatment apparatus of claim 1, wherein the foam body comprises polyurethane.

12. The wound treatment apparatus of claim 1, wherein the first and second series of curved apertures are in an arrangement that describes a circumference of a circle.

13. The wound treatment apparatus of claim 1, wherein one or more of the plurality of gaps of the first and second series of apertures is from 1.5 mm to 4 mm in length.

14. The wound treatment apparatus of claim 1, wherein the plurality of gaps of the first series of apertures separates each aperture from adjacent apertures in the first series of apertures, and the plurality of gaps of the second series of apertures separates each aperture from adjacent apertures in the second series of apertures.

15. The wound treatment apparatus of claim 1, wherein the perforated foam layer is configured to transfer contractile forces to a wound site to promote wound closure.

16. A wound dressing, comprising:
   a perforated contact layer;
   the perforated foam layer of claim 1; and
   a cover layer.

17. The wound treatment apparatus of claim 1, wherein the plurality of curved apertures of the second series of apertures are arranged in an end to end pattern along a curved path that is spaced apart from the curved path of the first series of apertures.

18. A perforated foam layer for use in a negative pressure wound therapy dressing, comprising:
   a foam body; and
   a first series of slits extending all the way through the foam body, wherein:
      the first series of slits comprises a plurality of curved slits arranged in an end to end pattern;
      the first series of slits has a plurality of gaps between each of the plurality of curved slits where the material is left uncut; and
      each of the plurality of curved slits of the first series of slits forms an aperture in the foam body;
   a second series of slits extending all the way through the foam body;
   wherein:
      the second series of slits comprises a plurality of curved slits arranged in an end to end pattern;
      the second series of slits has a plurality of gaps between each of the plurality of curved slits where the material is left uncut;
      each of the plurality of curved slits of the second series of slits forms an aperture in the foam body; and
      the plurality of curved slits of the second series of slits are offset from the plurality of curved slits of the first series of slits so that each of the curved slits of the second series of slits is staggered relative to each of the curved slits of the first series of slits and so that each of the gaps of the second series of slits is staggered relative to each of the gaps of the first series of slits;
      wherein, when the foam layer is in an initial conformation, the plurality of curved slits of the first series of slits are arranged along a first curved path and the plurality of curved slits of the second series of slits are arranged along a second curved path.

19. A wound dressing for use in a negative pressure wound therapy apparatus, comprising:
   a perforated contact layer;
   the perforated foam layer of claim 18;
   a cover layer; and
   a tube configured to supply a source of negative pressure to a space beneath the wound dressing.

20. The perforated foam layer of claim 18, further comprising a third series of slits extending all the way through the foam body, wherein:
   the third series of slits comprises a plurality of curved slits arranged in an end to end pattern;
   the third series of slits has a plurality of gaps between each of the plurality of curved slits where the material is left uncut;
   each of the plurality of curved slits of the third series of slits forms an slit in the foam body; and
   the plurality of curved slits of the third series of slits are offset from the plurality of curved slits of the second series of slits so that each of the curved slits of the third series of slits is staggered relative to each of the curved slits of the second series of slits and so that each of the gaps of the third series of slits is staggered relative to each of the gaps of the second series of slits.

21. A perforated foam layer for use in a wound dressing, comprising:
   a foam body; and
   a first series of curved apertures extending through the foam body;
   a second series of curved apertures extending through the foam body;
   wherein:
      the first series of curved apertures comprises a plurality of spaced-apart curved apertures;
      the first series of curved apertures has a plurality of gaps between each of the plurality of spaced-apart curved apertures where the material is left uncut;
      the second series of curved apertures comprises a plurality of spaced-apart apertures; and
      the second series of curved apertures has a plurality of gaps between each of the plurality of spaced-apart curved apertures where the material is left uncut;
      wherein the first series of curved apertures are arranged along a first curved path and the second series of curved apertures of the second series of slits are arranged along a second curved path when the foam layer is in an initial conformation.

22. The perforated foam layer of claim 21, wherein the plurality of spaced-apart curved apertures of the second series of curved apertures are staggered relative to the plurality of spaced-apart curved apertures of the first series of curved apertures.

23. The perforated foam layer of claim 21, further comprising a third series of apertures extending all the way through the foam body, wherein:
   the third series of apertures comprises a plurality of curved apertures arranged in an end to end pattern;
   the third series of apertures has a plurality of gaps between each of the plurality of curved apertures where the material is left uncut;
   each of the plurality of curved apertures of the third series of apertures forms an aperture in the foam body; and
   the plurality of curved apertures of the third series of apertures are offset from the plurality of curved apertures of the second series of apertures so that each of the curved apertures of the third series of apertures is staggered relative to each of the curved apertures of the second series of apertures and so that each of the gaps of the third series of apertures is staggered relative to each of the gaps of the second series of apertures.

* * * * *